US008680140B2

(12) United States Patent
Brinton et al.

(10) Patent No.: US 8,680,140 B2
(45) Date of Patent: *Mar. 25, 2014

(54) PHYTOESTROGENIC FORMULATIONS FOR ALLEVIATION OR PREVENTION OF MENOPAUSAL SYMPTOMS

(75) Inventors: Roberta Diaz Brinton, Rancho Palos Verdes, CA (US); Liqin Zhao, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 477 days.

This patent is subject to a terminal disclaimer.

(21) Appl. No.: 12/606,006

(22) Filed: Oct. 26, 2009

(65) Prior Publication Data

US 2010/0113586 A1 May 6, 2010

Related U.S. Application Data

(63) Continuation-in-part of application No. 11/777,951, filed on Jul. 13, 2007.

(60) Provisional application No. 60/819,849, filed on Aug. 2, 2006, provisional application No. 60/889,920, filed on Feb. 14, 2007, provisional application No. 60/943,190, filed on Jun. 11, 2007, provisional application No. 61/108,126, filed on Oct. 24, 2008, provisional application No. 61/112,382, filed on Nov. 7, 2008.

(51) Int. Cl.
*A61K 31/35* (2006.01)

(52) U.S. Cl.
USPC .......................................................... 514/454

(58) Field of Classification Search
USPC .......................................................... 514/454
See application file for complete search history.

(56) References Cited

U.S. PATENT DOCUMENTS

| | | | |
|---|---|---|---|
| 5,952,374 A | 9/1999 | Clarkson, Jr. et al. | |
| 6,335,038 B1* | 1/2002 | Cavazza | 424/757 |
| 2004/0072765 A1 | 4/2004 | Kelly et al. | |
| 2004/0106561 A1* | 6/2004 | Kelly | 514/27 |
| 2005/0004360 A1 | 1/2005 | Gayo-Fung | |
| 2005/0058709 A1* | 3/2005 | Fisher et al. | 424/468 |
| 2005/0245492 A1* | 11/2005 | Lephart et al. | 514/170 |
| 2008/0108696 A1 | 5/2008 | Brinton et al. | |

FOREIGN PATENT DOCUMENTS

| | | |
|---|---|---|
| EP | 0 149 551 | 7/1985 |
| JP | 2001523258 | 11/2001 |
| JP | 2002542286 | 11/2002 |
| JP | 2006504409 | 2/2006 |
| WO | WO 94/23716 | 10/1994 |
| WO | 9850026 | 11/1998 |
| WO | 0064438 | 11/2000 |
| WO | WO 02/051821 | 7/2002 |
| WO | 2004009035 | 1/2004 |
| WO | WO 2005/089567 | 9/2005 |

OTHER PUBLICATIONS

Zhao et al. Structure-Based Virtual Screening for Plant-Based ER-B-Selective Ligands as Potential Preventative Therapy against Age-Related Neurodegenerative Diseases. J. Med. Chem. 48, pp. 3463-3466 (2005).*
Morito et al. Interaction of Phytoestrogens with Estrogen Receptors a and b (II). Biol. Pharm. Bull. 25(1), pp. 48-52 (2002).*
Kinjo et al. Interactions of Phytoestrogens with Estrogen Receptors a and b (III). Biol. Pharm. Bull. 27(2) pp. 185-188 (2004).*
Avis, et al, "Is there a menopausal syndrome? Menopausal status and symptoms across racial/ethnic groups", *Soc. Sci. Med.*, 52(3):345-56 (2001).
Brinton, et al, "Impact of estrogen therapy on Alzheimer's disease: a fork in the road?" *CNS Drugs*, 18(7):405-422 (2004).
Bromberger, et al, "Psychologic distress and natural menopause: a multiethnic community study", *Am. J. Public Health*, 91(9):1435-42 (2001).
Brookmeyer, et al., "Projections of Alzheimer's disease in the United States and the public health impact of delaying disease onset", *Am. J. Public Health*, 88(9):1337-42 (1998).
Cohen, et al, "Risk for new onset of depression during the menopausal transition: the Harvard study of moods and cycles" *Arch. Gen. Psychiatry*, 63(4):385-90 (2006).
DaSilva and Van Lier, "Synthesis and structure-affinity of a series of 7 alpha-undecylestradiol derivatives: a potential vector for therapy and imaging of estrogen-receptor-positive cancers", *J. Med.* 1990.

(Continued)

*Primary Examiner* — Jeffrey S. Lundgren
*Assistant Examiner* — Sara E Townsley
(74) *Attorney, Agent, or Firm* — Pabst Patent Group LLP

(57) ABSTRACT

Select phytoestrogen pharmaceutical compositions and methods of use for preventing or reducing one or more symptoms associated with pre menopause, menopause, and/or post menopause are described herein. These select phytoestrogen formulations are composed only of two or more plant-derived estrogenic molecules and/or their structural analogues and exhibit binding preference to ERβ over ERα and agonist activity in the brain. These ERβ-selective phytoestrogen formulations cross the blood-brain-barrier and promote estrogen-associated neurotrophism and neuroprotection mechanisms in the brain, without activating proliferative mechanisms in the reproductive tissues and are therefore devoid of other estrogen-associated problematic aspects. The formulations can be administered enterally, transdermally, transmucosally, intranasally or parenterally. The formulations preferably contain combinations of compounds, and can be formulated for daily, sustained, delayed or weekly/monthly administration. In a preferred embodiment, these are administered to women who are in menopause or post menopausal, most preferably early in menopausal.

7 Claims, 16 Drawing Sheets

(56) References Cited

OTHER PUBLICATIONS

Espeland, et al, "Conjugated equine estrogens and global cognitive function in postmenopausal women: Women's Health Initiative Memory Study", *JAMA*, 29(24):2959-68 (2004).
Freeman, et al, "Associations of hormones and menopausal status with depressed mood in women with no history of depression", *Arch. Gen. Psychiatry*, 63(4):375-82 (2006).
Freeman, et al, "Hormones and menopausal status as predictors of depression in women in transition to menopause" *Arch. Gen. Psychiatry*, 61(1):62-70 (2004).
Gao, et al., "The relationships between age, sex, and the incidence of dementia and Alzheimer disease: a meta-analysis", *Arch. Gen. Psychiatry*, 55(9):809-15 (1998).
Gustafsson, et al, "What pharmacologists can learn from recent advances in estrogen signaling" *Trends Pharmacol Sci.*, 24(9):479-85 (2003).
Henderson, et al, "Postmenopausal hormone therapy and Alzheimer's disease risk: interaction with age", *J. Neurol. Neurosurg. Psychiatry*, 76(1):103-5 (2005).
Hogervorst, et al, "Hormone replacement therapy for cognitive function in postmenopausal women", *Cochrane Database Syst. Rev.*, 3):CD003122. (2002).
Kreijkamp-Kaspers, et al, "Effect of soy protein containing isoflavones on cognitive function, bone mineral density, and plasma lipids in postmenopausal women: a randomized controlled trial", *JAMA*, 292(1):65-74 (2004).
Manson, et al, "Postmenopausal hormone therapy: new questions and the case for new clinical trials", *Menopause*, 13(1):139-47 (2006).
Meyers, et al, "Estrogen recptor-beta potency-selective ligands: structure-activity relationship studies of diarylpropionitriles and their acetylene and polar analogues", *J. Med. Chem.*, 44(24):4230-51 (2001).
Morrison, et al, "Lack of efficacy of estradiol for depression in postmenopausal women: a randomized, controlled trial" *Biol. Psychiatry*, 15;55(4):406-12 (2004).
North American Menopause Society, (2004) The menopause practice: a clinician's guide http://www.menopause.org/aboutmeno/overview/htm.
Resnick, et al, "Hormone therapy and risk of Alzheimer disease: a critical time", *JAMA*, 288(17):2170-2 (2002),
Schmidt, et al, "A longitudinal evaluation of the relationship between reproductive status and mood in perimenopausal women", *Am. J. Psychiatry*, 161(12):2238-44 (2004).
Schmidt, et al, "Estrogen replacement in perimenopause-related depression: a preliminary report", *Am J Obstet Gynecol.*, 183(2);414-20 (2000).
Schmidt, et al, "Mood, depression, and reporductive hormones in the menopausal transition" *Am. J. Med.*, 118 Suppl 126:54-8 (2005).
Shumaker, et al, "Conjugated equine estrogens and incidence of probable dementia and mild cognitive impairment in postmenopausal women: Women's Health Initiative Memory Study." *JAMA*, 291(24):2947-58 (2004).

Soares, et al, "Efficacy of estradiol for the treatment of depressive disorders in perimenopausal women: a double-blind, randomized, placeb-controlled trial" *Arch. Gen. Psychiatry*, 58(6):529-34 (2001).
Stauffer, et al, "Pyrazole ligands: structure-affinity/activity relationships and estrogen receptor-alpha-selective agonists" *J. Med. Chem.*, 43(26)4934-4947 (2000).
Sun, et al, "Molecular basis for the subtype discrimination of the estrogen receptor-beta-selective ligand, diarylpropionitrile" *Mol. Endocrinol.*, 17(2):247-58 (2003).
Usui, et al., "Pharmaceutical prospects of phytoestrogens", Endocrine Journal, 53(1):7-20 (2006).
Wassertheil-Smoller, et al, "Depression and cardiovascular sequelae in postmenopausal women. The Women's Health Initiative (WHI)" *Arch. Intern. Med.*, 156(3):289-98 (2004).
Weihua, et al, "Update on estrogen signaling", *FEBS Lett.*, 546(1):17-24 (2003).
Yaffe, et al, "Estrogen therapy in postmenopausal women: effects on cognitive function and dementia" *JAMA*, 279(9):688-95 (1998).
Zandi, et al, "Hormone replacement therapy and incidence of Alzheimer disease in older women: the Cache County Study", *JAMA*, 288(17):2123-29 (2002).
Zhao, et al, "Neuroprotective and neurotrophic efficacy of phytoestrogens in cultured hippocampal neurons", *Exp. Biol. Med. (Maywood)*, 27(7):509-19 (2002).
Zhao, et al. "*2004 Abstract Book; The Keystone Symposia: Nuclear Receptors: Steroid Sisters*", Keystone, CO; Feb. 2004.
Zhao, et al., "Design, synthes, and estrogenic activity of a novel estrogen receptor modulator—a hybrid structure of 17beta-estradiol and vitamin E in hippocampal neurons", *J. Med Chem.*, 50(18):4471-81 (2007). Epub Aug. 14, 2007.
Zhao, et al., "Estrogenic agonist activity of ICI 182,780 (Faslodex) in hippocampal neurons: implications for basic science understanding of estrogen signaling and development of estrogen modulators with a dual therapeutic profile", *J. Pharmacol. Exp. Ther.*, 319(3):1124-32 (2006). Epub Sep. 1, 2006.
Zweifel, et al, "A meta-analysis of the effect of hormone replacement therapy upon depressed mood" *Psychoneurendocrinology*, 22(3):189-212 (1997).
An, et al., "Estrogen receptor $^2$-selective transcriptional activity and recruitment of coregulators by phytoestrogens" , J Biol. Chem., 276(21)17808-14 (2001).
Kuiper, et al., "Interaction of estrogenic chemicals and phytoestrogens with estrogen receptor$^{2}$", Endocrinology, 139(10):4252-63 (1998).
Morito, et al., "Interaction of phytoestrogens with estrogen receptors ± and $^2$" , Biol. Pharm. Bull., 24(4):351-56 (2001).
Wakeling, et al., "A potent specific pure antiestrogen with clinical potential" , Cancer Res, 51:3867 (1991).
Kinjo,"Phytoestrogens" ,Nippon, Rinsho, 58(12):60-64 (2000).
Hedlund, et al., "Prostatic fluid concentrations of isoflavonoids in soy consumers are sufficient to inhibit growth of benign and malignant prostatic epithelial cells in vitro" , Prostate, 66(5):557-66 (2006).

* cited by examiner

Test Compounds
- ■ Progesterone
- ▲ 17β-Estradiol
- ▼ Genistein
- ◆ Daidzein
- ● Equol
- × IBSO03569
- + G + D
- ✱ G + D + E
- ׀ G + D + E + I

*P<0.05, **P<0.01 Compared to OVX Control Group

*P<0.05,**P<0.01 Compared to OVX Control Group

*P<0.05 Compared to OVX Control Group

*P<0.05, **P<0.01 Compared to OVX Control Group

*P<0.05, **P<0.01 Compared to OVX Control Group

PHYTOESTROGENIC FORMULATIONS FOR ALLEVIATION OR PREVENTION OF MENOPAUSAL SYMPTOMS

CROSS-REFERENCE TO RELATED APPLICATIONS

This application is claims priority to U.S. Ser. No. 11/777,951, filed on Jul. 13, 2007, which claims priority to U.S. Ser. No. 60/819,849 filed on Aug. 1, 2006; U.S. Ser. No. 60/889,920 filed Feb. 14, 2007, and U.S. Ser. No. 60/943,190 filed Jun. 11, 2007. This application also claims priority to U.S. Ser. No. 61/108,126 filed on Oct. 24, 2008, and U.S. Ser. No. 61/112,382 filed on Nov. 7, 2008. The disclosures in the applications listed above are incorporated by reference.

FIELD OF THE INVENTION

This invention is in the field of pharmaceutical compositions for the treatment or prevention of premenopausal, menopausal, and/or postmenopausal symptoms.

BACKGROUND OF THE INVENTION

The demographics suggest that we face a devastating increase in the prevalence of Alzheimer's disease (AD), reinforcing the immediate need for basic and translational neuroscience to develop safe and efficacious estrogen therapy (ET) and hormone therapy (HT) regimens for the brain. Of those affected with AD, 68% are female and 32% are male (Brookmeyer et al., 1998 Am J Public Health 88:13372). Because women have a longer life expectancy than men, the absolute number of women with AD exceeds that of men. However, a double danger exists for women. Results of a meta-analysis of seven sex-specific studies concluded that women are 1.5 times more likely to develop AD than age-matched men (Gao et al., 1998 Arch Gen Psychiatry 55:809), which was supported by the Cache County analysis that showed a clear female gender increase in the incidence of AD (Zandi et al., 2002 JAMA 288:21239).

At the turn of the new millennium in the United States, there were nearly 42 million women over the age of 50 years and, of these, more than 31 million women were over the age of 55 years (North American Menopause Society, 2004). Worldwide, there are currently more than 470 million women aged 50 years or older, and 30% of those are projected to live into their 80s (North American Menopause Society, 2004). These women can anticipate spending one-third to one-half of their lifetime in the menopausal state. Reports on the prevalence of AD vary, but of the 18 million American women in their mid to late 70s, as many as 5 million may suffer from AD, and this figure increases dramatically at older ages (Brookmeyer et al., 1998). The projected exponential increase in the prevalence of AD, along with the anticipated impact on families and society, highlights the imperative for developing strategies to prevent or delay the onset of AD sooner rather than later.

The profound disparities between the largely positive basic science findings of gonadal steroidal action in brain and the adverse outcomes of recent ET/HT clinical trials in women who are either aged postmenopausal or postmenopausal with AD, has led to an intense reassessment of gonadal hormone action and the model systems used in basic and clinical science. One key factor that could contribute to the negative results of the Women's Health Initiative Memory Study ("WHIMS") trial was the advanced age, more than ten years following menopause, at which ET/HT was initiated in women. Data from both basic science analyses and clinical studies indicate a "healthy cell bias" of estrogen action in the neurons/brains, suggesting that ET/HT acts as an effective preventative therapeutic strategy for age-related cognitive decline and neurodegenerative disorders, such as Alzheimer's disease ("AD"), while it is not an effective treatment strategy. The current widely prescribed ET, conjugated equine estrogens ("CEE"), is a highly complex ET with over 200 different components. Whether CEE provides the optimal therapeutic efficacy has been questioned. Another key issue challenging HT is the optimal composition. For example, the use of progestin, and its timing of administration in conjunction with ET, remains to be determined. Moreover, while ET/HT has long been used in postmenopausal women to delay or reverse some of the problems associated with menopause, epidemiological and clinical studies have uncovered potential long-term risks related to this therapy. The recently revealed risks associated with ET/HT have greatly increased interest in the development of estrogen alternatives that promote beneficial effects of estrogen in brain, bone and the cardiovascular system, while not eliciting deleterious effects in other organs, particularly in breast and uterine tissues.

Two nuclear receptors for estrogen (ERs), ERα and ERβ, have been identified. In the central nervous system, both ERα and ERβ are expressed in the hippocampus and cortex of rodent and human brains. Previous studies have demonstrated that both ERα and ERβ can equivalently promote neuronal survival by activating estrogen mechanisms of action in rat hippocampal neurons. Increasing evidence indicates that ERβ is a key requirement for activation of mechanisms that underlie estrogen-inducible neuronal morphological plasticity, brain development, and cognition. ERα, on the other hand, is more predominant in mediating the sexual characteristics of estrogen effects in the reproductive organs such as breast and uterus. Taken together, these data establish a potential therapeutic application for ERβ as a pharmacological target to promote memory function and neuronal defense mechanisms against age-related neurodegeneration such as Alzheimer's disease (AD), while avoiding activating untoward estrogenic proliferative effects in the breast and uterus, although this might be at the cost of lower efficacy due to the lack of activation of ERβ in the brain. Other potential therapeutic advantages associated with ERβ include regulation of estrogen vasculoprotective action and development of interventions targeting diseases such as depression, colon cancer, prostate cancer, obesity, leukemia, and infertility. However, a potential disadvantage of an ERβ-selective ligand is the lack of activation of ERα in bone, as ERα has been demonstrated to mediate estrogen regulation of bone density.

In searching for an effective ERβ-selective estrogen alternative replacement therapy for promoting neurological function and preventing age-related neurodegeneration, such as AD, in postmenopausal women, it is of particular interest to identify and develop naturally occurring molecules or analogues that potentially have a less toxic profile for long-term administration. It is known that several plant-derived estrogenic molecules (referred to as "phytoestrogens") bind to ERα and to ERβ subtypes, and some of these molecules possess moderate binding selectivity for ERβ and exert estrogenic effects in multiple tissues.

The therapeutic efficacy of phytoestrogens in the brain remains controversial. On the one hand, when administered singly, phytoestrogens appeared to be moderately neuroprotective (Zhao, et al., *Exp. Biol. Med.*, 227, 509-519 (2002). On the other hand, a recent clinical trial revealed that a soy protein supplement that contains a mixture of phytoestrogens did not show improved cognitive function in postmenopausal women, when treatment was initiated at the age of 60 years or older. (Kreijkamp-Kaspers, et al. *JAMA* 2004, 292, 65-74). As discussed previously, when started 10 or more years following menopause in postmenopausal women when age-related neuronal reorganization had taken place, ET/HT has no benefit on neural function. Therefore, it can be extrapolated that age and hormonal "history" may also be important factors regulating the actions of phytoestrogens in the brain, as was the case for the WHIMS trials.

Another issue that can substantially impact the efficacy of phyto-estrogen mixtures in the brain is the formulation of phytoestrogens. Soy extracts or soy protein supplements generally contain multiple phytoestrogenic molecules, some of which may be ERα-selective agonists, while others may be ERβ-selective agonists, and others may be ineffective in activating either ERα or ERβ but may function as inhibitors of ER binding of those ERα and/or ERβ phytoestrogenic agonists.

ERα and ERβ have a yin/yang relationship in many contexts where one receptor may antagonize the actions of the other (Weihua, et al. *FEBS Lett.* 2003, 546, 17-24; Gustafsson, J. A. *Trends Pharmacol. Sci.* 2003, 24, 479-485). Studies confirmed this observation, showing that coadministration of ERα-selective agonist PPT and ERӨ-selective agonist DPN was less efficacious than either PPT or DPN alone in protecting hippocampal neurons against excitotoxic insults. These findings indicate that although both ERα and ER contribute to estrogen promotion of neuronal survival, simultaneous activation of both ER subtypes, ERα and ERβ, in the same context may diminish the efficacy. Accordingly, a presumption can be made that, in addition to the ER antagonism, the ineffectiveness of administering a mixture of phytoestrogens (i.e. a soy protein supplement) may also partly come from the antagonizing actions among different phytoestrogens, which may be ERα selective or ERβ selective.

Development of an ERβ-selective phytoestrogen formulation could maximize the therapeutic benefits associated with activation of ERβ in the brain while minimizing the adverse effects associated with the activation of ERα in reproductive tissues. Moreover, selective targeting of ERβ potentially reduces antagonistic actions that may occur in a complex soy-derived preparation. This naturally occurring ideal formulation would have tremendous therapeutic value in promoting neurological function and preventing AD in a population at risk for losing neurological capacity and losing memory function, i.e., postmenopausal women. To date, no such phytoestrogen formulation exists. Thus, there is a need for select phytoestrogen formulation, generally, and particularly, a formulation that functions in the brain.

It is therefore an object of the present invention to provide an ERβ-selective phytoestrogen formulation maximizing the therapeutic benefits associated with activation of ERβ in the brain while minimizing the adverse effects associated with the activation of ERα in reproductive tissues.

It is a further object of the invention to provide such a composition wherein the active ingredients are isolated from natural substances.

It is further an object of the invention to provide compositions to prevent one or more symptoms associated with menopause or postmenopause and methods of making and using thereof.

SUMMARY OF THE INVENTION

Select phytoestrogen pharmaceutical compositions and methods of use for promoting and/or sustaining neurological health and preventing age-related neurodegenerative diseases, such as AD, have been developed. These select phytoestrogen formulations are composed of a number of plant-derived estrogenic molecules and/or their structural analogs and exhibit binding preference to ERβ over ERα and agonist activity in the brain. These ERβ-selective phytoestrogen formulations cross the blood-brain-barrier and promote estrogen-associated neurotrophism and neuroprotection mechanisms in the brain, without activating proliferative mechanisms in the reproductive tissues, and are therefore devoid of estrogen-associated problematic aspects. The select phytoestrogen formulations are therapeutically useful to both women and men.

The compositions are administered enterally, transdermally, transmucosally, intranasally or parenterally, in a dosage effective to prevent or alleviate neuronal damage, promote neuronal regeneration or sustain viability, enhance expression of anti-apoptotic mechanisms, and/or decrease indicators of AD. The composition can also be administered to prevent and/or minimize one or more symptoms associated with menopause including, but not limited to, hot flashes, hot flushes, hair loss/thinning, mood changes, insomnia, fatigue, memory problems, and combinations thereof. The compositions may also be useful to prevent hair loss/thinning in men as well as to reduce the risk of prostate cancer in men. The compositions can be formulated for daily, sustained, delayed or weekly/monthly administration. In a preferred embodiment, these are administered to women who are in menopause or post menopausal, most preferably early in menopause.

BRIEF DESCRIPTION OF THE DRAWINGS

FIG. 2A illustrates 17-β-Estradiol (E2), acting via a membrane-associated site (mER), activates a cascade required for multiple responses that lead to enhanced neural plasticity, morphogenesis, neurogenesis, and neural survival. FIG. 2B illustrates estrogen-induced neuroprotective mechanisms convergence on mitochondria.

FIG. 7E is a graph of percent increase in mitochondrial respiratory activity for the different groups.

FIG. 5E is a graph of percent increase in mitochondrial COX activity.

FIG. 10A is a graph showing the results of a Y-maze two-trial recognition test of spatial working memory function for OVX mice treated with the phytoSERMs-containing diet and a soy-extract diet versus an OVX control. FIGS. 10B-D are graphs showing the percent levels of brain-derived neurotrophic factor (BDNF) (FIG. 10B), synaptophysin (FIG. 10C), and SPD-95 (FIG. 10D), respectively, as a function of diet. FIGS. 10E and 10F are graphs showing the percent levels of IDE (FIG. 10E) and NEP (FIG. 10F) as a function of diet.

DETAILED DESCRIPTION OF THE INVENTION

I. Definitions

Figure 1:
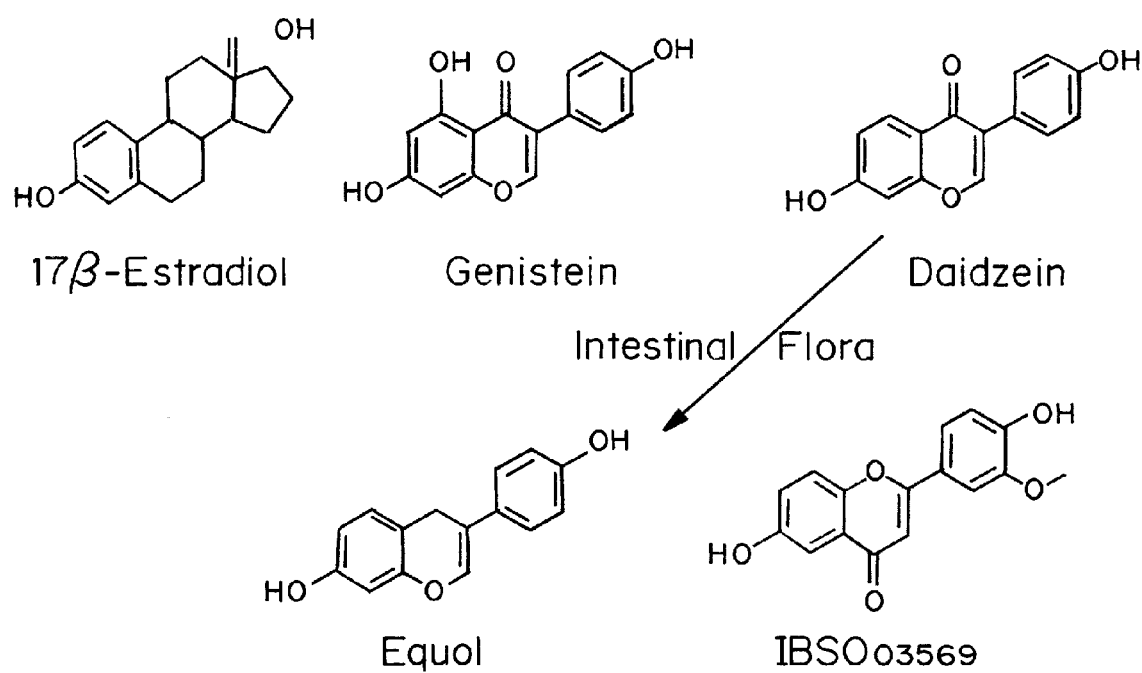
FIG. 1 shows the chemical Structures of 17β-estradiol and the phytoSERMs genistein, daidzein, equol, and IBSO03569.

"Estrogen Receptor", as used herein, refers to any protein in the nuclear receptor gene family that binds estrogen, including, but not limited to, any isoforms and variants thereof. Human estrogen receptors include the alpha- and beta-isoforms (referred to herein as "ERα" and "ERβ").

"Estrogen Receptor Modulator", as used herein, refers to a compound that can act as an estrogen receptor agonist or antagonist of an estrogen receptor or estrogen receptor isoform having an $IC_{50}$ or $EC_{50}$ with respect to ERα, ERβ and/or other estrogen receptor isoforms of no more than about 50 μM as determined using the ERα, and/or ERβ transactivation assay described herein. More typically, estrogen receptor modulators have $IC_{50}$ or $EC_{50}$ values (as agonists or antagonists) of not more than about 10 μM. Representative compounds are predicted to exhibit agonist or antagonist activity via an estrogen receptor. Compounds preferably exhibit an antagonist or agonist $IC_{50}$ or $EC_{50}$ with respect to ERα and/or ERβ of about 10 μM, more preferably, about 500 nM, even more preferably about 1 nM, and most preferably, about 500 pM, as measured in the ERα and/or ERβ transactivation assays. "$IC_{50}$" is that concentration of compound which reduces or inhibits the activity of a target (e.g., ERα or ERβ) to half-maximal level. "$EC_{50}$" is that concentration of compound which provides half-maximum effect.

"Selective Estrogen Receptor Modulator" (or "SERM"), as used herein, refers to a compound that exhibits activity as an agonist or antagonist of an estrogen receptor (e.g., ERα, ERβ or other estrogen receptor isoform) in a tissue-dependent or receptor dependent manner. Thus, as will be apparent to those of skill in the biochemistry, molecular biology and endocrinology arts, compounds that function as SERMs can act as estrogen receptor agonists in some tissues, e.g., bone, brain, and/or cardiovascular, and as antagonists in other tissue types, e.g., the breast and/or uterine tissue.

"Phytoestrogen" refers to a naturally occurring compound of plants, such as soybeans, or plant products, such as whole grain cereals, that acts like estrogen or binds to an estrogen receptor.

As used herein, the term "PhytoSERM" refers to natural source phytoestrogens that preferentially target estrogen receptor beta.

As used herein, the term "analogue" refers to a chemical compound with a structure similar to that of another (reference compound) but differing from it in respect to a particular component, functional group, atom, etc.

As used herein, the term "derivative" refers to compounds which are formed from a parent compound by chemical reaction(s).

"Pharmaceutically acceptable salt", as used herein, refer to derivatives of the compounds defined by Formula I and II wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Modified release dosage form: A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release, extended release, and pulsatile release dosage forms and their combinations are types of modified release dosage forms.

Delayed release dosage form: A delayed release dosage form is one that releases a drug (or drugs) at a time other than promptly after administration.

Extended release dosage form: An extended release dosage form is one that allows at least a twofold reduction in dosing frequency as compared to the drug presented as a conventional dosage form (e.g. as a solution or prompt drug-releasing, conventional solid dosage form).

Pulsatile release dosage form: A pulsatile release dosage form is one that mimics a multiple dosing profile without repeated dosing and allows at least a twofold reduction in dosing frequency as compared to the drug presented as a conventional dosage form (e.g. as a solution or prompt drug-releasing, conventional solid dosage form). A pulsatile release profile is characterized by a time period of no release (lag time) or reduced release followed by rapid drug release.

II. Compositions

Compositions containing one or more phytoestrogens are described herein. A number of phytoestrogens have been isolated and identified and additional analogs created, all of which have estrogen receptor binding selectivity. In one embodiment, the composition contains two or more plant-derived estrogenic molecules and/or structural analogues, which possess ERβ-binding selectivity and exhibit neuroprotective activity when administered individually. These compositions are useful for preventing estrogen-deficiency associated symptoms and disorders, particularly age-related cognitive decline and neurodegenerative diseases, such as Alzheimer's disease ("AD"). The compositions are also useful for minimizing or preventing one or more symptoms of menopause including, but not limited to, hot flashes, hair loss/thinning, mood changes, insomnia, fatigue, memory problems, and combinations thereof. The compositions may also be useful to prevent and/or reduce hair loss/thinning in men. The compositions may also be useful to prevent or treat prostate cancer in men.

A. PhytoSERMs

The compositions described herein contain one or more phytoestrogens or natural source selective estrogen receptor modulators (SERMs) exhibiting a binding preference for ERβ. PhytoSERMs can be identified as described in Example 1. Suitable phytoSERMs include, but are not limited to, genistein, daidzein, equol, IBSO03569 and combinations thereof. The structures of genistein, daidzein, equol, and IBSO03569 are shown in FIG. 1. Other potential phytoSERMs are listed in Table 1 in Example 1. Preferred phytoSERMs are those that cross the blood brain barrier. As demonstrated in Example 2, combinations of two or more PhytoSERMs are more effective than administration of one PhytoSERM.

The compounds can be used in the form of salts derived the parent acid or base. The salts can be prepared using organic or inorganic acids or bases. Suitable salts include, but are not limited to, acetate, adipate, alginate, citrate, aspartate, benzoate, benzenesulfonate, bisulfate, butyrate, camphorate, camphorsulfonate, digluconate, cyclopentanepro-pionate, dodecylsulfate, ethanesulfonate, glucoheptanoate, glycerophosphate, hemi-sulfate, heptanoate, hexamate, fumarate, hydrochloride, hydrobromide, hydroiodide, 2-hydroxyethanesulfonate, lactate, maleate, methanesulfonate, nicotinate, 2-napthalenesulfanate, oxalate, pamoate, pectinate, sulfate, 3-phenylpropionate, picrate, pivalate, propionate, succinate, tartrate, thiocyanate, p-toluenesulfonate and undecanoate. Also, any basic nitrogen-containing groups can be quaternized with agents such as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Wafer or oil-soluble or dispersible products are thereby obtained.

Examples of acids which may be employed to form pharmaceutically acceptable acid addition salts include such inorganic acids as hydrochloric acid, sulfuric acid, and phosphoric acid, and organic acids such as oxalic acid, maleic acid, succinic acid and citric acid. Basic addition salts can be prepared in situ during the final isolation and purification of the compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, and aluminum salts, as well as non-toxic ammonium, quaternary ammonium, and mine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, and piperazine.

The compounds described herein may have one or more chiral centers and thus exist as one or more stereoisomers. Such stereoisomers can exist as a single enantiomer, a mixture of diastereomers or a racemic mixture.

As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

B. Additional Active Agents

While the compounds can be administered as the sole active pharmaceutical agent, they can also be used in combination with one or more other compound as described herein, and/or in combination with other agents used in the treatment and/or prevention of estrogen receptor-mediated disorders. Alternatively, the compounds can be administered sequentially with one or more such agents to provide sustained therapeutic and prophylactic effects. Suitable agents include, but are not limited to, other SERMs as well as traditional estrogen agonists and antagonists.

Representative agents useful in combination with the compounds for the treatment of estrogen receptor-mediated disorders include, for example, tamoxifen, 4-hydroxytamoxifen, raloxifene, toremifene, droloxifene, TAT-59, idoxifene, RU 58,688, EM 139, ICI 164,384, ICI 182,780, clomiphene, MER-25, DES, nafoxidene, CP-336,156, GW5638, LY 139481, LY353581, zuclomiphene, enclomiphene, ethamoxytriphetol, delmadinone acetate, bisphosphonate. Other agents that can be combined with one or more of the compounds include aromatase inhibitors such as, but not limited to, 4-hydroxymdrostenedione, plomestane, exemestane, aminogluethimide, rogletimide, fadrozole, vorozole, letrozole, and anastrozole.

Still other agents useful in combination with the compounds described herein include, but are not limited to antineoplastic agents, such as alkylating agents, antibiotics, hormonal antineoplastics and antimetablites. An example includes the compounds used to treat or prevent osteoporosis. Other ingredients include vitamins, nutritional supplements, anti-oxidant agents, coenzymes, etc.

The additional active agents may generally be employed in therapeutic amounts as indicated in the PHYSICIANS' DESK REFERENCE (PDR) 53rd Edition (2003), or such therapeutically useful amounts as would be known to one of ordinary skill in the art. The compounds and the other therapeutically active agents can be administered at the recommended maximum clinical dosage or at lower doses. Dosage levels of the active compounds in the compositions may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

C. Pharmaceutical Compositions

The compounds can be combined with one or more pharmaceutically acceptable carriers, additives, and/or excipient for enteral, transdermal, transmucosal, intranasal, or parenteral administration. The compounds can also be administered via a transdermal patch, a depo, vaginally or rectally using a topical carrier such as a gel, lotion, ointment, liposomal formulation, suspension, foam, spray or suppository, via the pulmonary or nasal route, buccally or sublingual via the mucosal membranes of the mouth. The carriers, additives, and/or excipients are all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of coating compositions which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides. Additionally, the coating material may contain conventional carriers such as plasticizers, pigments, colorants, glidants, stabilization agents, pore formers and surfactants.

Excipients for oral formulation are known to those skilled in the art, as discussed briefly below, and can be used to provide immediate, sustained, delayed, pulsed release, and combinations thereof. For parenteral administration, the compounds may be dissolved or suspended in saline, sterile water or phosphate buffered saline, or a suitable oil for injection intravenously (iv), intramuscularly (im), subcutaneously (subcu), intrasternal, infusion, or intraperitoneal (ip).

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-.beta.-cyclodextrin, polyvinylpyrrollidone, low melting waxes, and ion exchange resins, as well as combinations of any two or more thereof. Other suitable pharmaceutically acceptable excipients are described in Remington's Pharmaceutical Sciences, Mack Pub. Co., New Jersey (1991).

Pharmaceutical compositions containing estrogen receptor modulating compounds may be in any form suitable for the intended method of administration, including, for example, a solution, a suspension, or an emulsion. Liquid carriers are typically used in preparing solutions, suspensions, and emulsions. Liquid carriers contemplated for use include, for example, water, saline, pharmaceutically acceptable organic solvent(s), pharmaceutically acceptable oils or fats, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, surfactants, or stabilizers. Suitable organic solvents include, for example, monohydric alcohols, such as ethanol, and polyhydric alcohols, such as glycols. Suitable oils include, for example, soybean oil, coconut oil, olive oil, safflower oil, cottonseed oil. For parenteral administration, the carrier can also be an oily ester such as ethyl oleate, isopropyl myristate. Compositions may also be in the form of microparticles, microcapsules, liposomal encapsulates, as well as combinations of any two or more thereof.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate;

and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The compounds may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water; Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifing and suspending agents, cyclodextrins, and sweetening, flavoring, and perfuming agents.

The compounds can also be administered in the form of lipsomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound, stabilizers, preservatives, excipients. The preferred lipids are the phospholipids and phosphatidyl cholines (lecithins), both natural and synthetic. Methods to form liposomes are known in the art (Prescott 1976).

Transdermal patches are well known for delivery of nicotine, nitroglycerin and birth control. These can be utilized with these formulations as well. Depos that are implanted under the skin or ip can also be used, similarly to the manner of delivering birth control.

Appropriate carriers can be incorporated that assist the compounds to cross the blood-brain-barrier.

Modified Release Dosage Forms

The compounds can also be formulated for modified release, such as delayed release, sustained release, pulsatile release, and combinations thereof.

Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release

The formulation can provide pulsatile delivery of the one or more neuro-protective agents. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to S hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

III. Methods of Administration

Compounds can be administered in a variety of ways including enteral, parenteral, pulmonary, nasal, mucosal and other topical or local routes of administration. For example, suitable modes of administration include oral, subcutaneous, transdermal, transmucosal, iontophotetic, intravenous, intramuscular, intraperitoneal, intranasal, subdural, rectal, vaginal and inhalation.

An effective amount of the compound or composition is administered to treat and/or prevent an estrogen receptor-mediated disorder in a human or animal subject. Modulation of estrogen receptor activity results in a detectable suppression or up-regulation of estrogen receptor activity either as compared to a control or as compared to expected estrogen receptor activity. Effective amounts of the compounds generally include any amount sufficient to delectably modulate estrogen receptor activity by any of the assays described herein, by other activity assays known to those having ordinary skill in the art, or by detecting prevention and/or alleviation of symptoms in a subject afflicted with an estrogen receptor-mediated disorder.

The amount of active ingredient that may be combined with the carrier materials to produce a single dosage form will vary depending upon the estrogen-mediated disease, the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes, a prophylactically or therapeutically effective dose will generally be from about 0.01 mg/kg/day to about 100 mg/kg/day, preferably from about 0.1 mg/kg/day to about 20 mg/kg/day, and most preferably from about 1 mg/kg/day to about 10 mg/kg/day of a estrogen receptor modulating compound, which may be administered in one or multiple doses.

The effective amount will also be determined based on when the compounds are administered. Estrogen/hormone therapy (ET/HT) has been associated with the reduced risk of developing AD when treated at the menopausal transition in women Brinton, R. D. Impact of estrogen therapy on Alzheimer's disease: a fork in the road? *CNS Drugs* 2004, 18, 405-422. For example, results of the Cache County Study indicate that women who receive ET/HT at the time of menopause and continue for 10 years have a 3-fold lower risk of developing AD, Zandi, et al. *JAMA* 2002, 288, 2123-2129, whereas the recent data from the Women's Health Initiative Memory Study indicate that women who begin the therapy late in menopause have a greater risk of developing AD, Espeland, et al. Women's Health Initiative Memory Study. *JAMA* 2004, 291, 2959-2968; Shumaker, et al., *JAMA* 2004, 291, 2947-2958. These clinical observations are consistent with basic science analyses of estrogen-inducible molecular mechanisms in the brain, indicating a healthy cell bias of estrogen action.

Estrogen receptor-mediated disorders that may be treated include any biological or medical disorder in which estrogen receptor activity is implicated or in which the inhibition of estrogen receptor potentiates or retards signaling through a pathway that is characteristically defective in the disease to be treated. The condition or disorder may either be caused or characterized by abnormal estrogen receptor activity. Representative estrogen receptor-mediated disorders include, for example, osteoporosis, atherosclerosis, estrogen-mediated cancers (e.g., breast and endometrial cancer), Turner's syndrome, benign prostate hyperplasia (i.e., prostate enlargement), prostate cancer, elevated cholesterol, restenosis, endometriosis, uterine fibroid disease, hot flashes, and skin and/or vagina atrophy. Other estrogen receptor-mediated conditions that may be treated include neurological diseases and disorders including memory loss and dementia, and neurodegenerative disease, including Alzheimer's disease. The compositions may also be used to treat one or more symptoms associate with the various stages of menopause including, but not limited to, hot flashes, hot flushes, hair loss/thinning, mood changes, insomnia, fatigue, memory problems, and combinations thereof. The composition may also be useful in treating hair loss/thinning in men.

In addition to the potential beneficial effects of estrogen on episodic memory, some evidence suggests that HT reduced the risks of both dementia (including AD) and mild cognitive impairment (MCI). MCI is a condition thought to represent a transitional state between normal cognition and dementia in some individuals, with a 12% conversion rate from MCI to dementia each year. Observational studies repeatedly document that women taking HT enjoy an 30% reduced risk for dementia compared with women not taking HT [odds ratio range, 0.306 (Yaffe et al., 1998 JAMA 279:688; Hogervorst et al., 2003 Cochrane Database Syst Rev CD003122)]. Thus, observational studies suggest that declining reproductive function could be a modifiable risk factor for dementia or that HT/ET could serve a protective role against some of the risks for developing dementia.

Several recent observational studies have identified that the stage of reproductive aging at which HT/ET is started modifies the risk of dementia. In these studies, women who take HT/ET during the late menopause transition or early postmenopause have a lower risk of dementia than those starting HT/ET later (Zandi et al., 2002 JAMA 288:21239; Henderson et al., J Neurol Neurosurg Psychiatry 76:103 2005). Thus, the timing of starting HT/ET relative to the menopause has been proposed to be one factor explaining the otherwise discordant observations between the observational studies and the RCTs (Resnick and Henderson, 2002 JAMA 288:21702; Manson et al., 2006 Menopause 13:139). Recent preclinical studies reviewed below highlight the importance of timing of ET in this report.

Successful treatment of a subject may result in the prevention, inducement of a reduction in, or alleviation of symptoms in a subject afflicted with an estrogen receptor-mediated medical or biological disorder. Thus, for example, treatment can result in a reduction in breast or endometrial tumors and/or various clinical markers associated with such cancers. Treatment of Alzheimer's disease can result in a reduction in rate of disease progression, detected, for example, by measuring a reduction in the rate of increase of dementia.

Historically, there has been a presumption that declining reproductive function plays no role in the onset of mood disorders that occur during midlife in women. The symptoms of depression during the menopause transition also were assumed to be transient and of such minor severity that they were dismissed to be of little clinical consequence. Recent studies, however, suggest that these presumptions are incorrect. First, several community-based longitudinal studies have reported the relative independence of depressions during the menopause transition and hot flushes: both occur at this stage of life, but depression is not simply caused by hot flushes (Avis et al., 2001 Soc Sci Med 52:345). Second, recent longitudinal studies that followed women with no past history of depression demonstrated an increased risk of first-onset depressions during the late menopause transition (Schmidt et al., 2004 Am J Psychiatry 161:22384; Cohen et al., 2006 Arch Gen Psychiatry 63:385; Freeman et al., 2006 Arch Gen Psychiatry 61:62). Finally, both major and minor depressions are clinically significant to women at midlife, because both are associated with an increased risk for several other medical conditions (Wassertheil-Smoller et al., 2004 Arch Intern Med 164:289) relevant to the health of women at midlife (e.g., cardiovascular disease, dementia, and the metabolic syndrome).

The majority of women do not develop depression during the menopause transition, and, therefore, reproductive aging is not uniformly associated with either depressive symptoms or the syndrome of depression. Nonetheless, despite numerous studies concluding that the menopause is not associated with an increased risk for developing depression in women, several other longitudinal, community-based studies reported an association between the menopause transition and an increased risk for depression (Schmidt, 2005 Am J Med 118: 54). Indeed, five recent longitudinal studies all have documented an increased risk for depression during the menopause transition, with odds ratios ranging from 1.8 to 2.9 compared with the premenopause (Bromberger et al., 2001 Am J Public Health 91:14352; Freeman et al., 2004 Arch Gen Psychiatry 61:62, 2006 Arch Gen Psychiatry 63:375; Schmidt et al., 2004 Am J Psychiatry 161:22384; Cohen et al., 2006 Arch Gen Psychiatry 63:385). These data suggest that events surrounding the final menstrual period may predispose some women to develop clinically significant depressive illness. Although several factors could precipitate depression in these women, endocrine events are suggested by the stage of the menopause transition (i.e., late) during which depressions appeared. The late transition is characterized by more prolonged hypogonadism than the early perimenopause, during which estradiol secretion may be increased. Thus, the timing of appearance of the depressions observed suggest an endocrine mechanism related to the perimenopause (estradiol withdrawal and/or recent-onset of prolonged hypogonadism) in the pathophysiology of perimenopausal depression.

Efforts to investigate the potential role of declining ovarian hormone secretion in the onset of depression have examined the effects on mood of administering HT/ET in women with perimenopausal and postmenopausal depression. The antidepressant efficacy of estradiol has been examined in three relatively recent RCTs of women meeting standardized diagnostic criteria for major and minor depression, who were randomly assigned to enter double-blind, placebo-controlled trials (Schmidt et al., 2000; Soares et al., 2001 Arch Gen Psychiatry 58:529; Morrison et al., 2004 Biol Psychiatry 55:406). In perimenopausal women, short-term administration (3 weeks) of estradiol significantly decreased depression scores compared with both baseline and placebo conditions. In one study, a full or partial therapeutic response was seen in 80% of perimenopausal women on estradiol compared with 22% of those on placebo (Schmidt et al., 2000). The efficacy of ET in perimenopausal depression is consistent with the observed effect size (0.69) in a recent meta-analysis of studies examining the effects of estrogen on mood (Zweifel and O'Brien, 1997 Psychoneuroendocrinology 22:189). The therapeutic response to estradiol was observed in both major and minor depression as well as in women with and without hot flushes. Thus, the efficacy of ET in perimenopausal depression is not solely a product of its ability to reduce the distress of hot flushes. In contrast to these studies in perimenopausal depression, the administration of estradiol under similar conditions failed to improve mood in depressed women who were 5 years postmenopause (Morrison et al., 2004). Thus, the effects of estradiol on depression may be limited to perimenopausal women. Additionally, as with the potential effects of estrogen on the course of dementia, the stage of reproductive aging at which women present and/or commence ET might modify the observed outcomes.

In summary, the majority of women do not develop depression during or after the menopause transition. Nevertheless, recent prospective studies monitoring both reproductive status and mood have documented that, for some women, perimenopause-related events increase the risk for the onset of depression. The role of ovarian function in these episodes of depression is suggested by both the timing of their onset relative to the last menstrual period and the antidepressant efficacy of short-term ET.

An ER β-Selective Phytoestrogenic Formulation Exerts Enhanced Effects on Neuronal Survival and Brain Defense Mechanisms Against AD Pathogenesis In the examples described below, a series of in vitro to in vivo comparative analyses of 1) ERα/β binding profile, 2) neuroprotective efficacy, 3) regulation of brain mitochondrial bioenergetics and anti-apoptotic protein expression, 4) regulation of brain Aβ-degrading protein expression, and 5) impact on uterine growth, induced by four ERβ-selective and clinically relevant phytoestrogens, when used alone or in combination were conducted. Results from these analyses indicate that an ERβ-selective phytoestrogenic formulation can exert enhanced effects on neuronal survival and brain defense mechanisms associated with prevention of neurodegenerative diseases, particularly AD pathogenesis.

An ERα/β binding analysis revealed a heterogeneous profile from individual phytoestrogens with respect to their intrinsic binding affinity and selectivity to ERα and ERβ, which was modifiable when used in combination. Genistein exhibited the maximal binding affinity to both ERS, particularly to ERβ (~41% of 17β-estradiol), followed by equol (~14% of genistein), daidzein (~34% of equol) and IBSO03569 (~22% of daidzein). However, their binding selectivity for ERβ followed a disparate order: IBSO03569 (>100-fold)>genistein (~60-fold)>daidzein (~14-fold) >equal (~10-fold). The combination of genistein with daidzein (G+D), or daidzein and equol (G+D+E), or daidzein, equol and IBSO03569 (G+D+E+I), yielded a 50% or greater decrease in the ERβ-binding affinity, at ~50%, 41% and 30% of genistein for G+D, G+D+E and G+D+E+I, respectively. Nevertheless, the ERβ-binding selectivity of these combinations remained the same or was increased compared to genistein. Combinations of G+D and G+D+E+I exhibited a similar ERβ selectivity to genistein, at ~63-fold and 61-fold, respectively. In comparison, G+D+E exhibited a ~30% greater selectivity for En (~83-fold) than genistein. These results indicate that addition of an ERβ weak ligand in a formulation could induce a competitive binding to the same site and lead to a decrease in the overall binding affinity. However, such a reduction in the binding affinity could be offset by a substantial increase in the ERβ-binding selectivity.

An enhanced effect resulting from a rational combination of ERβ-selective phytoestrogens was first demonstrated in the in vitro analyses of the neuroprotective efficacy against degenerative insults in cultured rat primary hippocampal neurons. Results indicate that despite individual ER-selective phytoestrogens efficacy to promote neuronal membrane integrity against glutamate insult, only genistein was sufficient to induce a significant increase in neuronal metabolic viability against the insult. There was no evident enhancement observed for the combination of G+D, which in fact did not generate a significant effect. In comparison, the combination of G+D+E not only induced a significantly increased neuronal metabolic viability against glutamate insult when compared to neurons treated with genistein (P<0.05), it was also highly protective in both neuronal membrane integrity and metabolic viability against the aggregated $A\beta_{1-42}$. Although neurons treated with the combination of G+D+E+I also exhibited an enhanced viability against both glutamate and $A\beta_{1-42}$ insult, the overall magnitude was lower than neurons treated with G+D+E. In particular, following $A\beta_{1-42}$ exposure, metabolically live cells were significantly higher in cultures treated with G+D+E than those treated with G+D+E+I (P<0.05). These analyses indicate that select, but not all, combinations of ERβ-selective phytoestrogens can provide an enhanced effect on promotion of neuronal survival. These results argue against the postulate that randomly increasing the number of different phytoestrogens in a formulation will lead to a greater efficacy. Moreover, a random mixture is more likely to generate antagonistic interactions resulting in decreased efficacy. Enhancement from select combinations of ERβ-selective phytoestrogens was also evident in vivo. In ovariectomized adult female rats, treatment with the combination of G+D+E, at a clinically relevant dosage, significantly enhanced brain mitochondrial bioenergetics, as evidenced by increased respiratory efficiency and COX enzymatic activity. In comparison, animals treated with genistein alone at the same dosage did not exhibit a significant change in RCR, although there was an increase but at a much lower magnitude relative to G+D+E in COX enzymatic activity. In both measurements, the effect induced by G+D+E was significantly greater than genistein alone (P<0.05). Consistent with in vitro neuroprotection, the magnitude of change induced by G+D+E+I was lower than that induced by G+D+E, although there was no significant difference between the two formulations. The enhanced mitochondrial respiration was paralleled by significantly increased expression of mitochondrial anti-apoptotic proteins, Bcl-2 and Bcl-xL. Efficacy of induction of Bcl-2 and Bcl-xL was comparable across 17β-estradiol, genistein and G+D+E, whereas G+D+E+I was relatively ineffective. While genistein was ineffective at enhancing mitochondrial respiratory activity, genistein did significantly increase the expression of both Bcl-2 and Bcl-xL, with an efficacy on par with that of 17β-estradiol and G+D+E. These results may suggest a dissociation between regulation of gene products, Bcl-2 and Bcl-xL, and activation of signaling cascades that regulate mitochondrial bioenergetic function. It appeared that induction of Bcl-2 and Bcl-xL was well correlated with the ERβ-binding affinity, which, however, was not the main determinant of brain mitoenergetic function. Moreover, combinations of G+D+E and G+D+E+I exerted a marked effect on the expression of two intraneuronal Aβ-degrading enzymes, IDE and NEP. It was noted that G+D+E induced an increase in NEP expression significantly greater than that induced by 17β-estradiol (P<0.01). For genistein alone, there was no change in the expression of IDE although there was a significant increase in the expression of NEP but at a much lower magnitude than those induced by either 17β-estradiol or G+D+E (P<0.01). Consistent with most of the observations presented in the examples, G+D+E was more efficacious than the combination of G+D+E+I. Together, these data support a role of an ERβ-selective phytoestrogenic formulation in promoting brain defense mechanisms against deficits in mitochondrial function and anti-apoptotic protein expression and deficits in Aβ catabolism, both of which have been associated with an increased risk of neurodegenerative diseases particularly AD. Although the combination of G+D+E or G+D+E+I exhibited an efficacy similar to 17β-estradiol in neural tissues, both formulations did not induce a significant impact on uterus. In comparison, 17β-estradiol induced a 2-fold increase in uterine weight under the same treatment paradigm. More impressively, the combination of G+D+E exerted an approximately 10% reduction in uterine weight relative to vehicle-treated control animals. Although there was not a significant difference between two groups, such a slight decline could become apparent upon a long-term use leading to a preventive effect against reproductive cancers. Collectively, the examples indicate that an improved ERβ-binding selectivity can be achieved by a select combination of ERβ-selective phytoestrogens. Moreover, an ERβ-selective phytoestrogenic formulation can produce enhanced effects on neuronal survival and brain defense mechanisms against neurodegeneration and AD, while remaining safe in reproductive tissues.

An ER β-selective Phytoestrogenic Formulation Offers Therapeutic Advantages Over a Soy-Derived Extract An ERβ-selective phytoestrogenic formulation, exemplified by the combination of G+D+E, potentially offers several therapeutic advantages. Mechanistically, the strategy to selectively target ERβ is anticipated to achieve three main goals. First, it has been widely demonstrated that ERα and ERβ play a differential role in reproductive tissues. ERα serves as the primary mediator of estrogen-inducible sexual modulation and proliferative responses, whereas ERβ has a much smaller impact on these biological processes. Therefore, selective activation of ERβ presents an opportunity to promote the estrogenic specificity in the brain while minimizing the adverse effects in the uterus and breast as seen with the conventional estrogen-containing HT. An ER strategy that lacks feminizing effects can potentially benefit men as well (e.g., treatment of hair loss/thinning). Second, our previous work in primary neuronal cultures revealed that co-administration of an ERα-selective agonist and an Eβ-selective agonist was less effective than treatment with either single agonist to induce a neuroprotective response, suggesting that simultaneous activation of both ERα and ERβ by their cognate agonists in the same context may diminish the efficacy. This observation is speculated to relate to the formation of heterodimers as opposed to homodimers induced by 17β-estradiol. Accordingly, in a formulation composed of multiple ligands, selective activation of ERβ avoids the potential antagonism occurring in a mixture comprising activators of both ERα and ERβ. Third, in addition to the therapeutic domain shared by an ERα or ERβ-selective agonist, an ERβ therapy has been suggested to have its own unique therapeutic advantages. In particular, activation of ERβ could potentially down-regulate apolipoprotein E4 (ApoE4), one major risk factor for acquiring AD. Conversely, activation of ERα could upregulate ApoE4. Therefore, an ERβ-selective therapy could be particularly beneficial to ApoE4 allele carriers, a population susceptible to AD.

Clinically, an Eβ-selective phytoestrogenic formulation, G+D+E, addresses the compositional complexity and potential antagonism present in a soy extract. Soy-derived extracts are the most common form used in phytoestrogen intervention studies. However, variations in the phytoestrogen composition could be significant among extracts derived from various sources of soy plants and manufactured based upon different protocols. An analysis of 33 commercial soy extracts revealed that there was an abundance of peaks of unknown origin found in many of the extracts. Although the bioactivity of these unknown molecules remains undefined, their potential impact on human health cannot be neglected. A complex formulation containing a mixture of various phytoestrogenic molecules could induce either an enhanced or antagonistic effect depending on the composition and interactions among these molecules. First, an antagonistic interaction in a complex formulation could be induced by molecules that are antiestrogenic. Second, phytoestrogens generally possess a biphasic estrogenic and antiestrogenic activity depending on the dose, target tissue, and/or estrogen status in a mammalian system. Evidence indicates that some phytoestrogens tend to exert an estrogenic effect at relatively low doses, and shift to antiestrogenic or cytotoxic when doses increase. The dose of phytoestrogens could significantly impact the efficacy and safety as well. A low dose could be insufficient to induce a clinically significant effect. However, a high dose for a long-term treatment could raise safety concerns. Third, an antagonistic interaction present in a complex formulation could also occur between an ERα-selective against and an ERβ-selective agonist. Conceivably, the antagonism, which can occur in a complex formulation such as a soy-derived extract, may diminish the overall effect to yield undetectable clinical outcomes. In support of this postulate, in the examples, the addition of the fourth phytoestrogen (IBSO03569) to the combination of G+D+E, not only weakened the ERβ-binding affinity and selectivity, it negatively impacted the overall activity of G+D+E+I as compared to G+D+E. These analyses underlie a critical notion that the phytoestrogen composition in a complex formulation could significantly affect the outcomes. A formulation should be designed in a rational manner in order to maximize the therapeutic potential that could be translated into a clinically meaningful effect.

Another potential clinical advantage is that inclusion of equol in a phytoestrogenic formulation, G+D+E, addresses the interindividual variations in daidzein metabolism and could potentially benefit both equol producers and nonproducers. Soyderived isoflavones commonly exist as inactive but water-soluble glucosides (genistin and daidzin), which are converted to estrogenically active aglycons (genistein and daidzein) by intestinal glucosidases prior to absorption. Unlike genistein and daidzein, equol is not of plant origin, yet can be exclusively produced through the metabolism of daidzein catalyzed by intestinal microbial flora following the intake of soy products. Interestingly, wide variations in the ability to produce equol from daidzein metabolism exist between rodents and humans, and across human populations. It has been found that almost all rodents and monkeys can produce equol in large quantities, however, only about 20-35% of Western adults have such equol-producing phenotype. In comparison, there is a high prevalence, with an approximate 55-60% of Asian populations being equol-producers. In addition to the intrinsic metabolic environment, equol production can be affected by other external factors. One factor is the form in which daidzein exists in a soy product. In a soy food or product that is made from soy plants grown under normal conditions, daidzein along with other isoflavones are present mainly in the inactive sugar-conjugated glycoside forms. However, in a stress-processed soy food or product made from soy germ, daidzein along with other isoflavones exist mainly in the unconjugated hormonally active aglycons. A study by Setchell et al. demonstrated that equol appeared in the plasma of half of the women who ingested daidzin, the glucoside conjugate of daidzein, while it was not found in the plasma of the women who consumed daidzein. The dietary matrix can also be a regulating factor impacting the harboring of those intestinal microflora responsible for equol synthesis.

Since it was first identified in human urine, equol has been widely recognized for its highly potent estrogenic activity, largely through its strong binding to both ER subtypes (~10-fold binding preference for ERβ over ERα) that are roughly equal (for ERα) or secondary (for ERβ) to genistein. In contrast, its precursor, daidzein, binds to ERβ at an affinity one third of equal (~14-fold binding preference for ERβ over ERα). To demonstrate the substantial difference in the estrogenic activity between equol and daidzein, it was found that equol was the most potent inducer of transcriptional β-galactosidase expression, especially in cells transfected with ERα, among all test isoflavones. In comparison, daidzein only induced a very weak transcription. Therefore, it can be speculated that the equol-producing phenotype could serve as a critical modulator of human response to phytoestrogen treatment, with an enhanced clinical efficacy in equal-producers as compared to nonproducers. To date, a number of studies have confirmed this hypothesis. This hypothesis may also hold true for a strong link between the many health benefits associated with phytoestrogen intake and the high prevalence of equol-producing phenotype in Asian populations. The failure to consider the interindividual variations in equol-producing phenotype could be another major cause of the disparity in clinical outcomes across studies. One way to minimize these variations while attaining equal-inducible health effects in both phenotypes is to administer equal exogenously so that it can be accessible in both equal-producers and nonproducers.

Both in vitro and in vivo analyses demonstrated that combined use of select test phytoSERMs provided significantly increased efficacy in sustaining neuronal survival when challenged with neurotoxins, promoting expression of proteins as key players in neuroprotection and metabolism/clearance of β-amyloid in neurons/brain, and enhancing brain mitochondrial functions. In particular, combined use of genistein, daidzein and equal at an equivalent weight afforded the maximal efficacy comparable or greater than 17b-estradiol in neuronal/brain assays. In contrast, such a combination showed no impact on uterine weight, which however was markedly increased by 17b-estradiol.

The examples indicate that combined use of select ERβ-selective PhytoSERMs can be more therapeutically effective than single administrations and alternative combined formulations. In particular, the examples suggest the potential of the combination of genistein, daidzein and equal, at an equivalent weight, for prevention of neurodegeneration and AD, along with management of climacteric symptoms in postmenopausal women.

Figure 2A:
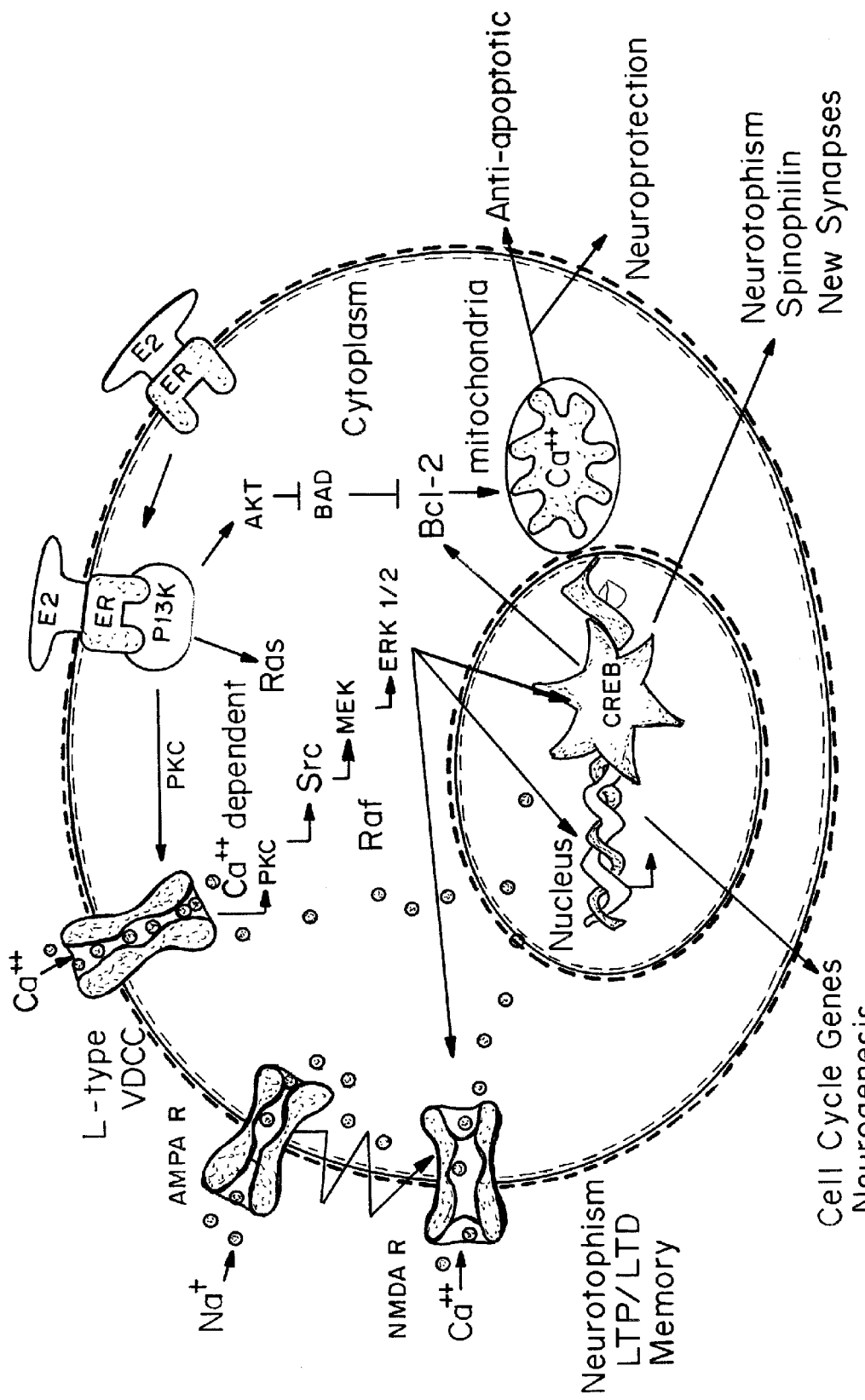
FIGS. 2A and 2B are schematics showing estrogen mechanisms of action that lead to neurotrophic and neuroprotective outcomes.
Figure 2B:
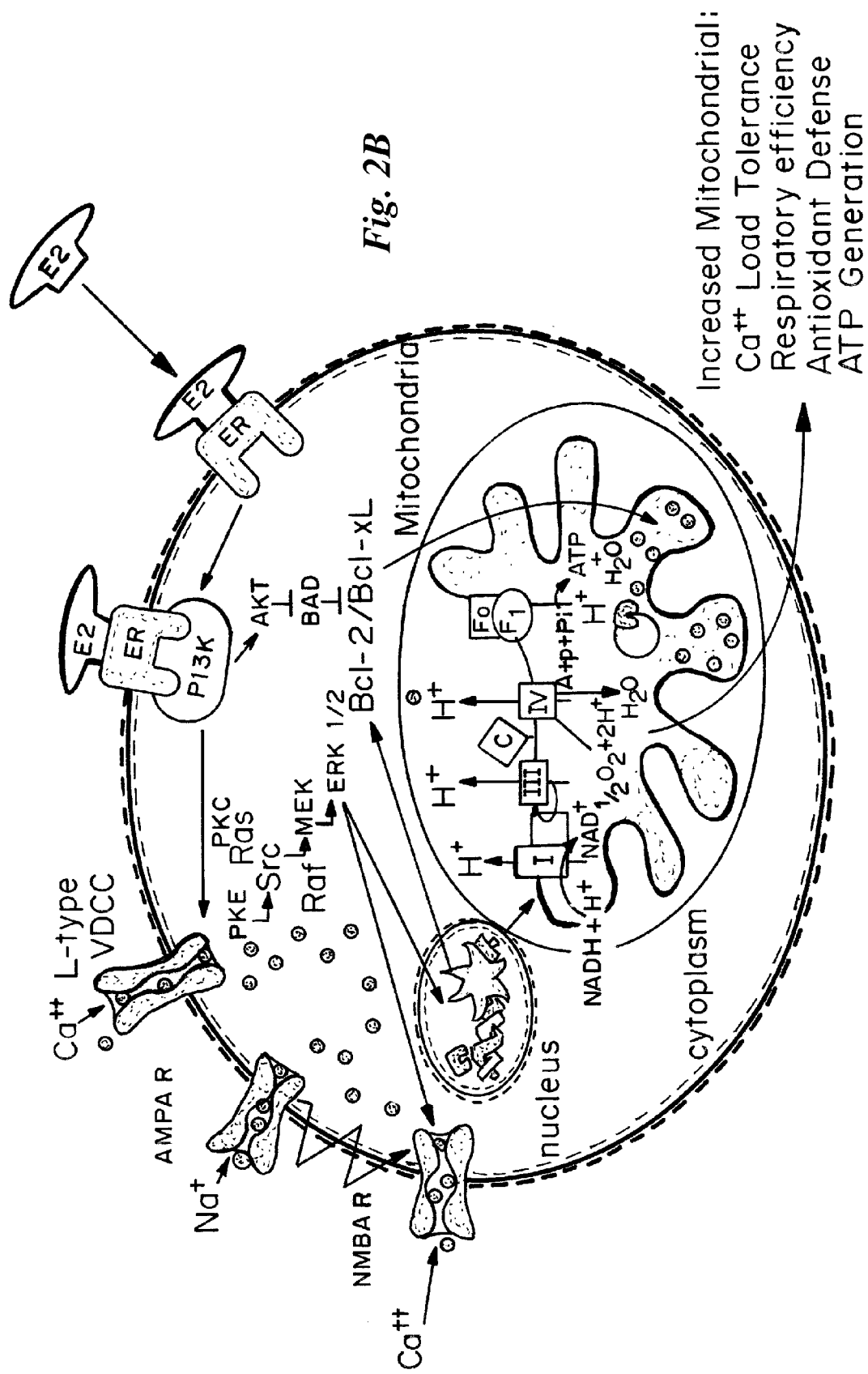

FIGS. 2A-2C are schematics showing estrogen mechanisms of action that lead to neurotrophic and neuroprotective outcomes. 17-β-Estradiol (E2) acting via a membrane-associated site (mER) activates a cascade required for multiple responses that lead to enhanced neural plasticity, morphogenesis, neurogenesis, and neural survival. The signaling sequence induced by E2 at the membrane site is as follows: (1) E2 binding to mER, (2) E2mER complexes with p85 to activate PI3K, (3) activating calcium-independent PKC, (4) phosphorylating the L-type calcium channel, (5) inducing calcium influx, (6) activating calcium-dependent PKCs, (7) activating Src kinase, (8) activating the MEK/ERK1/2 pathway, (9) ERK translocates to the nucleus, (10) activating and phosphorylating CREB, (11) enhancing transcription of anti-apoptotic genes Bcl-2 and Bcl-xl, which enhance mitochondrial vitality, and spinophilin, which encourages synaptic growth, (12) simultaneously, estrogen activation of PI3K leads to activation of Akt, which phosphorylates and inhibits the proapoptotic protein BAD.

Estrogen-induced neuroprotective mechanisms converge on mitochondria. Estrogen-activated cellular signaling cascade promotes enhanced mitochondrial function, leading to increased calcium load tolerance, enhanced electron transport chain efficiency, and promotion of antioxidant defense mechanisms. These actions are mediated by the regulation of both nuclear and mitochondrial encoded genes initiated by the activation of second-messenger signaling cascades.

Consistent with the healthy cell bias of estrogen benefit hypothesis, selective molecules would be administered before neurodegenerative insult while neurons are still healthy. phytoSERM exposure would lead to enhanced neural survival mechanisms, represented as mitochondria with Bcl-2 additions, that promote neural defense against neurodegenerative insults associated with age-associated diseases such as Alzheimer's and Parkinson's. Designer NeuroSERM molecules target the membrane site of estrogen action, whereas PhytoSERM molecules preferentially target estrogen receptorβ. Abbreviations: AMPAR, AMPA receptor; C, cytochrome oxidase; $F_0$, $F_1$, ATPase subunits; LTD, long-term depression; LTP, long-term potentiation; NAD, nicotinamide adenine dinucleotide; NADH, nicotinamide adenine dinucleotide; VDCC, voltage-dependent calcium channel.

These mechanisms and the data herein demonstrate that, consistent with the healthy cell bias of estrogen benefit hypothesis, selective molecules can be administered before neurodegenerative insult while neurons are still healthy and that phytoSERM exposure will lead to enhanced neural survival mechanisms, represented as mitochondria with Bcl-2 additions, that promote neural defense against neurodegenerative insults associated with age-associated diseases such as Alzheimer's and Parkinson's.

These studies exemplify the therapeutic promise of select ERβ-selective phytoestrogens when used in combination for sustaining memory function and preventing age-related neurodegenerative insults and AD. These ERR-selective phytoestrogen formulations, which optimize activation of ERβ while minimizing or avoiding activating ERα, should serve as an effective estrogen alternative replacement therapy for sustaining neurological health, function and prevention of AD without induction of proliferative responses in the reproductive tissues as seen with the current ET/HT. Moreover, in light of the most recent data indicating that activation of ERβ significantly reduces both ApoE mRNA and protein expression in neurons, ERβ-selective phytoestrogen formulations may serve as a particular viable strategy for reducing a major risk factor of AD in ApoE4 carriers.

IV. Kits

Kits may be provided which contain the formulation to be administered. The formulation may be administered once a day or more than once a day. The formulation can be administered enterally, parenterally, or topically. The kits typically contain the active agent(s) to be administered, excipients and carriers, and instructions for administration of the formulation. The kits may also contain equipment/devices used to administer the formulation, such as syringes.

The present invention will be further understood by reference to the following non-limiting examples.

EXAMPLES

Example 1

Identification of PhytoSERMs

ERβ has been associated with estrogen-induced promotion of memory function and neuronal survival. Based on the optimized complex structure of human ERβ LBD bound with genistein, computer-aided structure-based virtual screening against a natural source chemical database was conducted to determine the occurrence of plant-based ERβ-selective ligands. Twelve representative hits derived from database screening were assessed for their binding profiles to both ERs, three of which displayed over 100-fold binding selectivity to ERβ over ERα.

Materials and Methods

Identification of Compounds in Database

The ligand binding domains of the human ERα and ERβ are approximately 60% homologous. Structural modeling and mutational analyses indicate that two variant amino acid residues along the ligand binding pocket, Leu 384 and Met 421 in ERα, which are replaced with Met 336 and Ile 373, respectively, in ERβ, are the key molecular constituents underlying discriminative binding of selective ligands to either receptor subtypes. Sun, et al. *Mol. Endocrinol.* 2003, 17, 247-258. This slight structural variance serves as the foundation for both design and discovery of ER specific ligands. The similarities in the chemical features of both pairs of residues presents a substantial challenge to discover a selective ligand based on this difference. Of the known natural source ERβ-selective ligands, genistein remains the most selective. However, an increasing number of synthetic compounds are emerging showing greater selectivity than genistein for ERβ, as evidenced by the compound DPN developed in Katzellenebogen's laboratory. Computer-aided structure-based virtual database screening provides an efficient approach to rationally highlight a small group of lead candidates from a large number of compounds for investigation at the bench.

All computational work was performed on a SGI Octane workstation equipped with the IRIX 6.5 operating system (Silicon Graphic Inc.). First, the 3D crystallographic structure of human ERβ LBD complexed with genistein was downloaded from the Protein Data Bank (PDB ID: 1QKM). The complex structure was fixed and energy minimized with the Accelrys molecular modeling software package InsightII 2000 (Accelrys Inc.). An in-house 2D natural source chemical collection containing approximately 25 000 plant-based natural molecules or derivatives was converted to a 3D multiconformational database with the Accelrys modeling software package Catalyst 9.8 (Accelrys Inc.).

The receptor-docking site was defined based on the binding position of genistein in the receptor and specified as all atoms within 10 Å of the center carbon of genistein. GOLD 2.0 (Genetic Optimization for Ligand Docking), an automated ligand docking program distributed by CCDC (Cambridge Crystallographic Data Center), was applied to calculate and rank the molecules based on their complementarities with the receptor binding site, on both geometrical and chemical features.

Prior to the database screening, initial validation using genistein as the test ligand was conducted. The aim of the validation test was to evaluate the effectiveness of the algorithm of the docking program in identifying the experimentally observed binding mode of the ligand in the receptor, to determine whether the program is applicable to the specific target system in the examples. In addition, the validation test was used to determine the optimal parameter settings for the later database screening. Twenty docking runs were carried out on the test complex, using the fastest default generic algorithm parameters optimized for virtual library screening, and the GoldScore fitness function was applied. The validation test demonstrated that, based on the specified parameter settings, GOLD was effective in capturing the contributive hydrogen bond donor (ND1 in His 475) crucial to the binding and reproducing the nearly coincident solution in terms of both the binding orientation and conformation of genistein as observed in the experimental measurement (see FIG. 1). The root-mean-square (RMS) deviations were computed between the observed experimental position and the GOLD solutions, with RMSD 0.3299 and 0.4483 compared to top-ranked and worst solutions, respectively. The average RMSD of all solutions was 0.3566, which is regarded as a good prediction based on the subjective classifications defined by the program developer (refer to the program manual), suggesting that this program is reliable and applicable to the database screening toward ERβ.

Using the parameter settings determined in the validation test, the 3D natural source chemical database was input and docked into the prepared ERβ binding site in a flexible docking manner (full ligand and partial protein) and scored based on the GoldScore fitness function. Five hundred resultant top-scoring molecules were filtered via visual screening in the context of the receptor in InsightII. Based on visual analysis, 100 molecules underwent further analysis by Affinity, a more complex and predictive ligand docking program to refine the binding modes predicted by GOLD. The criteria used for the selection of candidate molecules for investigation included the following (a) formation of hydrogen bond with donor atom ND1 in His 475; (b) hydrophobic and hydrophilic balance appearing in the structure (e.g., the molecule should potentially have two relatively hydrophilic sides and a hydrophobic center to enhance both the steric and electrostatic complementarity with the receptor); (c) bound pose of the molecule in the receptor; and d) structural diversity. Finally, molecules that met the above criteria were computationally predicted for their drug-likeness (Lipinski's Rule of Five) and blood-brain barrier (BBB) penetration properties.

Determination of Binding Affinity and Selectivity

The binding affinity and selectivity of candidate molecules yielded from database screening were determined by a fluorescent polarization competitive binding assay using purified baculovirus-expressed human ERβ or ERβ and a fluorescent estrogen ligand EL Red (PanVera Corp.). Test molecules were serially diluted to a 2× concentration in assay buffer (200 μM to 200 μM). Fifty microliters of preincubated 2× complex of ERβ (30 nM) or ERβ (60 nM) and EL Red (2 nM) was added to each well in a 96-well Non-binding Surface black microplate (Corning Life Sciences) for a final volume of 80 or 100 μL. Negative controls containing ER and EL Red (equivalent to 0% inhibition) and positive controls containing only free EL Red (equivalent to 100% inhibition) were included. After a 2 hour or 6 hour incubation period at room temperature, the polarization values were measured using a Tecan GENios Pro reader at 535 nm/590 nm excitation/emission and plotted against the logarithm of the test molecule concentration. $IC_{50}$ values (concentration of test molecule that displaces half of the EL Red from ER) were determined from the plot using a nonlinear least-squares analysis available from GraphPad Prism Version 4.03 (GraphPad Software, San Diego, Calif.).

Results 31 molecules that can form a hydrogen bond with ND1 in His 475 were selected and grouped into three categories based upon the chemical features that favored both the van der Waals (VDW) contact (the number of the rings in the structure) and electrostatic interactions (the number of the hydrogen bonds) with the receptor. 10 molecules that have strong VDW interactions with the receptor, but without contributive hydrogen bonding, were grouped in Category IV. These molecules contain three or four five- or six-membered rings in their structures that could promote the hydrophobic interactions with the center of the receptor binding site as observed in endogenous estrogen 17β-estradiol that consists of four rings in its structure and binds to the estrogen receptor with a high affinity.

Table 1 summarizes the $IC_{50}$ binding results of test molecules to both ERα and ERβ as well as the binding selectivity of representative molecules selected from four categories.

TABLE 1

Binding Affinity ($IC_{50}$) and Selectivity of Representative Molecules for Estrogen Receptor α and β

| Compd | Structure | $IC_{50}$ ERα | $IC_{50}$ ERβ | Selectivity (ERα/ERβ) |
|---|---|---|---|---|
| Progesteron | 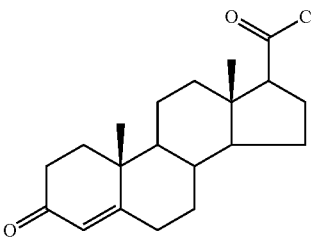 | NC* | NC | |
| genistein | 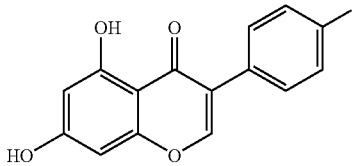 | 4.66 μM | 98.7 nM | 47.2 |
| 1 | 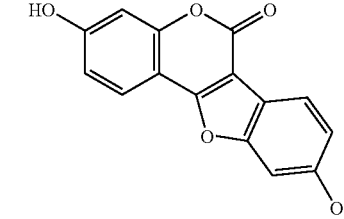 | 75.7 nM | 18.6 nM | 4.07 |
| 2 | 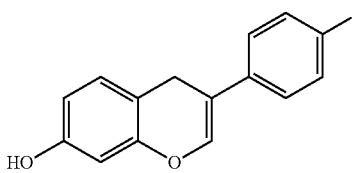 | NC | 0.68 μM | >100 |
| 3 | 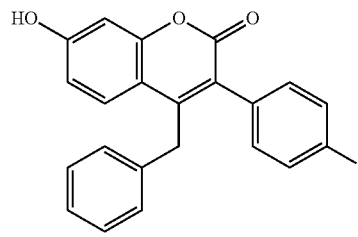 | 120 nM | 250 nM | 0.48 |

TABLE 1-continued

Binding Affinity (IC$_{50}$) and Selectivity of
Representative Molecules for Estrogen Receptor α and β

| Compd | Structure | IC$_{50}$ ERα | IC$_{50}$ ERβ | Selectivity (ERα/ERβ) |
|---|---|---|---|---|
| 4 | 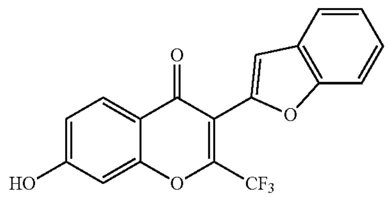 [SMILES: O=c1c(-c2cc3ccccc3o2)c(C(F)(F)F)oc2cc(O)ccc12] | NC | NC | |
| 5 | 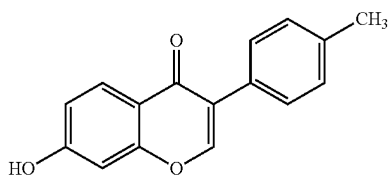 [SMILES: Cc1ccc(-c2coc3cc(O)ccc3c2=O)cc1] | NC | 2.80 μM | >100 |
| 6 | 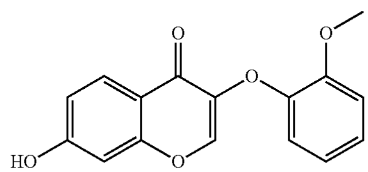 [SMILES: COc1ccccc1Oc1coc2cc(O)ccc2c1=O] | NC | NC | |
| 7 | 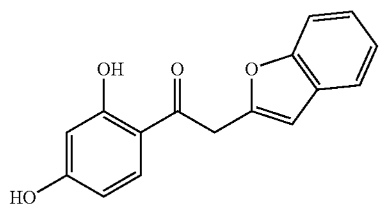 [SMILES: O=C(Cc1cc2ccccc2o1)c1ccc(O)cc1O] | 85.7 μM | 43.0 μM | 1.99 |
| 8 | 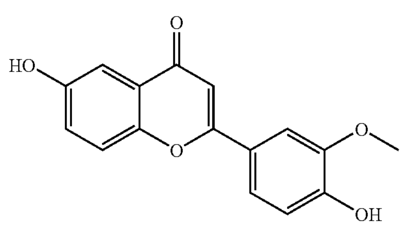 [SMILES: COc1cc(-c2cc(=O)c3cc(O)ccc3o2)ccc1O] | NC | 4.48 μM | >100 |
| 9 | 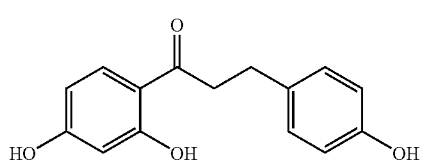 [SMILES: O=C(CCc1ccc(O)cc1)c1ccc(O)cc1O] | NC | NC | |
| 10 | 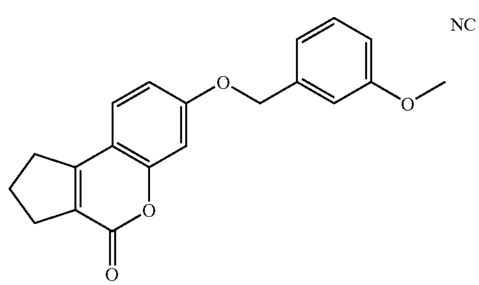 | NC | NC | |

TABLE 1-continued

Binding Affinity (IC$_{50}$) and Selectivity of
Representative Molecules for Estrogen Receptor α and β

| Compd | Structure | IC$_{50}$ ERα | IC$_{50}$ ERβ | Selectivity (ERα/ERβ) |
|---|---|---|---|---|
| 11 | [structure] | 2.32 µM | NC | <0.01 |
| 12 | [structure] | NC | NC | |

*NC: Noneconvergence within the dose range, predicting that either the molecule does not bind to the receptor or that the binding affinity is very low, with an IC$_{50}$ greater than 1 mM.

As expected, the negative control steroid, progesterone, does not bind to either ER. As a positive natural source estrogen control, genistein was found to bind to ERβ with a 47.2-fold greater binding selectivity over ERα, but at an affinity one-fourth of 17β-estradiol. Among 12 molecules tested, five molecules, 1, 2, 5, 7, and 8, showed binding selectivity to ERβ over ERα, 3 of which, 2, 5, and 8, displayed the selectivity over 100-fold. Preliminary structure and binding activity relationship analyses revealed that both the central hydrophobic skeletal structure and the connected two polar 'arms' contribute to the binding affinity of ligands to both ERs. The enhanced VDW contact derives mainly from the central hydrophobic feature of the molecule. For example, the number of rings increases the binding affinity of molecules to the receptor, as indicated by the VDW value of 17β-estradiol (−67.98) versus that of genistein (−60.75) and molecule 9 (−58.04), which are well correlated with their order-different binding affinities. Meanwhile, the hydrogen bonds derived from the two polar "arms" of the molecule are essential for the binding as well. The lack of one "arm" of the hydrogen bond, as represented by molecule 4 and 6, or two 'arms', as represented by 10 and 12, even though the latter two molecules can elicit strong VDW interactions with the receptor, with the VDW value of −72.58 and −69.19, respectively, leads to either very weak or no binding. With respect to the binding selectivity, as demonstrated in the modeling complex structures of a synthetic ERβ-selective agonist, PPT, Stauffer, et al. *J. Med. Chem.* 2000, 43, 4934-4947 and a synthetic ERβ-selective agonist, DPN, Meyers, et al., *J. Med. Chem.* 2001, 44, 4230-4251, with both ERs, Zhao, et al. 2004 *Abstract Book*; The Keystone Symposia: Nuclear Receptors: Steroid Sisters, Keystone, Colo.; February 2004, relatively larger molecular size favors the binding selectivity for ERβ over ERα, as represented by molecule 3 and 11.

These analyses shed light on the future search and design of more active and selective ER subtype-selective ligands. Further, 3 out of 12 representative molecules yielded from database searching displayed over 100-fold selectivity toward ERβ over ERα, demonstrating the effectiveness of this computer-aided virtual screening approach applied in the examples in the discovery of potential molecules that preferentially interact with ERβ.

Example 2

Preclinical Identification of ERβ-Selective PhytoSERM Combinations for Prevention of Neurodegeneration The impact of ERb-selective PhytoSERMs when administered singly or in combination on neuronal survival and molecular/functional markers associated with prevention of neurodegeneration and Alzheimer's disease (AD) was investigated.

Materials and Methods

17β-Estradiol was purchased from Steraloids (Newport, R.I.). Genistein, daidzein and equol were purchased from Indofine Chemical (Hillsborough, N.J.). IBSO03569 was purchased from InterBioScreen (Moscow, Russia). The structures of these compounds are shown in FIG. 1.

In Vitro Treatments: Test compounds (or combinations) were first dissolved in analytically pure DMSO (10 mM) and diluted in Neurobasal medium to the working concentrations right before treatments.

In Vivo Treatments: Test compounds (or combinations) were first dissolved in analytically pure DMSO and diluted in corn oil (50 ml of DMSO in 950 ml of corn oil) to the working concentrations at 100 mg/ml for 17β-estradiol and 10 mg/ml for phytoSERMs.

The use of animals was approved by the Institutional Animal Care and Use Committee at the University of Southern California (Protocol Number: 10780). Embryonic day 18 Sprague-Dawley rat (Harlan, Indianapolis, Ind.) fetuses were used to obtain primary hippocampal neuronal cultures for in vitro experiments. Young adult (14 to 16-week-old, weighing from 270-290 g) female ovariectomized Sprague-Dawley rats (Harlan) were used for in vivo experiments.

In Vitro Assays

ERα/β Competitive Binding Assays

The ERα/β binding profile of the test compounds or combinations were determined with a fluorescent polarization competitive binding assay (Invitrogen, Carlsbad, Calif.), as previously described. Test compounds or combinations (composed of equivalent molar of individual phytoestrogens included) were serially diluted to a 2× concentration in assay buffer (20 μM to 200 μM). 40 μL of assay buffer mixed with 2× test compounds or combinations were added to a 384-well non-binding surface microplate, followed by addition of 40 μL of preincubated 2× complex of ERα (30 nM) or ERβ (60 nM) and a fluorescent estrogen ligand EL Red (2 nM) for a final volume of 80 μL. After a 6-hr of incubation, the polarization values were measured using a GENios Pro microplate reader (Tecan, San Jose, Calif.) at excitation/emission 535/590 nm and plotted against the logarithm of the concentrations of the test compounds or combinations. $IC_{50}$ values were determined from the plot by a nonlinear least-squares analysis using GraphPad Prism Version 4.03 (GraphPad Software, San Diego, Calif.).

Assays to Assess Neuronal Function

Neuronal Culture Preparation

Primary cultures of hippocampal neurons were obtained from Embryonic Day 18 (E18) rat fetuses. Briefly, after dissected from the brains of the rat fetuses, the hippocampi were treated with 0.02% trypsin in Hank's balanced salt solution (137 mM NaCl, 5.4 mM KCl, 0.4 mM $KH_2PO_4$, 0.34 mM $Na_2HPO_4.7H_2O$, 10 mM glucose, and 10 mM HEPES) for 5 min at 37° C. and dissociated by repeated passage through a series of fire-polished constricted Pasteur pipettes. Between $2\times10^4$ and $4\times10^4$ cells were plated onto poly-D-lysine (10 μg/ml)-coated 22 mm coverslips in covered 35 mm petri dishes for morphological analysis, and $1\times10^5$ cells/ml were plated onto poly-D-lysine-coated 24-well, 96-well culture plates or $3-5\times10^5$ cells/ml onto 0.1% polyethylenimine-coated 60 mm petri dishes for biochemical analyses. Nerve cells were grown in phenol-red free Neurobasal medium (NBM, Invitrogen Corporation, Carlsbad, Calif.) supplemented with B27, 5 U/ml penicillin, 5 μg/ml streptomycin, 0.5 mM glutamine and 25 μM glutamate at 37° C. in a humidified 5% or 10% $CO_2$ atmosphere at 37° C. for the first 3 days and NBM without glutamate afterwards. Cultures grown in serum-free Neurobasal medium yielded approximately 99.5% neurons and 0.5% glial cells.

Neuroprotection Measurements

Glutamate Exposure

Primary hippocampal neurons were pretreated with compounds for 48 hr followed by exposure to 100 μM or 200 μM glutamate for 5 min at room temperature in HEPES buffer containing 100 mM NaCl, 2.0 mM KCl, 2.5 mM $CaCl_2$, 1.0 mM $MgSO_4$, 1.0 mM $NaH_2PO_4$, 4.2 mM $NaHCO_3$, 10.0 mM glucose and 12.5 mM T-LEPES. Immediately following glutamate exposure, cultures were washed once with HEPES buffer and replaced with fresh Neurobasal medium containing the test compounds. Cultures were returned to the culture incubator and allowed to incubate for 24 hr prior to cell viability measurements on the following day using lactate dehydrogenase (LDH) release measurement or calcein acetoxymethyl ester (AM) staining.

B-Amyloid$_{1-42}$ Exposure and Neuronal Viability

Fibrillar β-amyloid1-42 (American Peptide, Sunnyvale, Calif.) was prepared as described in the literature. Hippocampal neurons grown on 96-well culture plates for 7 DIV were pretreated with vehicle alone or test compounds for 48 hr, followed by exposure to freshly prepared 3 μM β-Amyloid1-42 in NBM in the presence of vehicle alone or test compounds at 37° C. for 3 days prior to neuronal viability analyses using a multiplex cytotoxicity assay (Promega, Madison, Wis.), which contains two fluorogenic peptide substrates allowing a simultaneous measurement of live and dead-cell protease activities. GF-AFC is a cell-permeant live-cell protease substrate and cleaved to generate a fluorescent signal proportional to the number of live cells in the cultures. Bis-AAF-R110 is a cellimpermeant dead-cell protease substrate and released from cells that have lost membrane integrity, therefore, it serves as a marker of cytotoxicity. Briefly, following β-Amyloid1-42 exposure, 80 μl of culture medium was kept in each well of the culture plate and 80 μl of the assay buffer mixed with two substrates was added to incubate at 37° C. for 45-60 min. The fluorescence intensities were measured on a SpectraMax dualwavelength-scanning microplate spectrofluorometer (Molecular Devices, Sunnyvale, Calif.) at excitation/emission filter combinations, 400/505 nm for live-cell fluorescence and 485/520 nm for deadcell fluorescence.

In Vivo Assays

Animal Treatment, Tissue Collection and Uterine Weight

Ovariectomized young adult female rats were placed on a phytoestrogen-reduced diet, TD.96155 (Harlan Teklad) during a 2-week recovery from the surgery prior to the treatment. Compounds were first dissolved in analytically pure DMSO and then diluted in corn oil (50 μl of DMSO in 950 μl of corn oil) to the working concentrations at 100 μg/ml for 17β-estradiol and 10 mg/ml for phytoestrogens. Combined formulations were composed of an equivalent amount of individual phytoestrogens included based upon the closeness of their molecular weight. Ovariectomized rats were treated, once daily for 2 d, with a subcutaneous injection of vehicle (control), 17β-estradiol (70 μg/kg BW), genistein (6 mg/kg BW), or phytoestrogen combinations (6 mg/kg BW). Following the second injection, animals fasted for 24 hr prior to sacrifice and brain dissection. Hippocampal and cortical tissues were collected from one hemisphere. The remaining brain tissues minus cerebellum, pineal gland, and brainstem were utilized for mitochondrial isolations. Uteri were excised, trimmed of fat and connective tissue, and a wet weight was recorded. The uteri were then air dried for 1 w and then at 70° C. overnight and the dry weight was recorded.

Forebrain Mitochondrial Isolation

Rat forebrain tissues were homogenized in mitochondrial isolation buffer (MIB: containing 320 mM sucrose, 10 mM Tris-HCl, 1 mM EDTA, pH 7.4-KOH) with freshly added 0.5 mg/ml-MIB of BSA and 10 μl/ml-MIB of protease inhibitor cocktail right before use, at 4° C. Homogenates were centrifuged at 1330×g for 5 min. Pellets were re-homogenized and centrifuged. The two postnuclear supernatants were combined and centrifuged at 21,200×g for 10 min. The resulting crude mitochondrial pellets were resuspended in 15% Percoll and layered over a 23%/40% discontinuous Percoll gradient and centrifuged at 31,000×g for 10 min. The fraction accumulating at the 23%/40% interface was collected and washed with 10 ml MIB by centrifugation at 16,700×g for 13 min. The pellets were then transferred to 1.5 ml Eppendorf tubes and centrifuged at 6,600×g for 8 min. The purified mitochondrial pellets were resuspended in MIB to an approximate concentration of 5 mg/ml. The purity and integrity of isolated mitochondria were confirmed as previously described (36). The isolated mitochondrial samples were used immediately for respiratory activity measurements or stored at −70° C. for enzymatic assays.

Mitochondrial Respiratory Activity

Mitochondrial respiratory activity was measured polygraphically using a Clarke-type oxygen electrode (Hansatech Osygraph) at 37° C. 100 μg of isolated mitochondria was added in a magnetically stirred chamber filled with 500 μl of respiration buffer (25 mM sucrose, 75 mM mannitol, 5 mM $KH_2PO_4$, 100 mM KCl, 0.05 mM EDTA, 20 mM HEPES, 5 mM $MgCl_2$, pH 7.4-KOH). After a basal respiration recording, mitochondrial state 4 respiration was measured following the addition of 10.5 μl of substrates, malate (2.5 mM)/glutamate (2.5 mM). State 3 respiration was measured following the addition of 2.5 it of ADP (350 μM). Respiratory control ratio (RCR) was calculated as the ratio between the rate of oxygen uptake at state 3 and the rate of oxygen uptake at state 4.

Mitochondrial Cytochrome C Oxidase Activity

Mitochondrial cytochrome c oxidase (COX) activity was measured using a microplate immunocapture method (MS427) developed by Mitosciences (Eugene, Oreg.), which spectrophotometrically monitors the change in absorbance at 550 nm following the oxidation of reduced cytochrome c. Briefly, COX in 25 μg of isolated mitochondria was first immunocaptured onto the assay plate, followed by the addition of the substrate, reduced cytochrome c. Colorimetric absorbance was measured at 550 nm at 30° C., and recorded every 5 min for 115 min, on a Benchmark Plus spectrophotometer equipped with a Microplate Manager Version 5.2 Build 103 software (Bio-Rad, Hercules, Calif.). Since the reaction is product inhibited, COX activity was expressed as the initial rate of oxidation of reduced cytochrome c, and determined by calculating the initial slope between two time points within the linear region (5-15 min).

Western Blot

Protein extraction and concentration determination were performed as previously described (26). 20-40 μg of protein samples were loaded per lane and separated by electrophoresis on 10-12% SDS-PAGE. Proteins were then electrotransferred to PVDF membranes and probed with primary antibodies against Bcl-2 (1:250, Zymed Laboratories, San Francisco, Calif.), Bcl-xL (1:500, Zymed Laboratories), or IDE (1:1000, Calbiochem), at 4° C. overnight and then with HRP-conjugated secondary antibodies (Vector Laboratories, Burlingame, Calif.). β-tubulin (Abcam, Cambridge, Mass.) was used as the loading control. Bands were visualized with a TMB peroxidase kit (Vector Laboratories) or by chemiluminescence using an ECL detection kit (Amersham, Piscataway, N.J.). Relative intensities of the immunoreactive bands were quantified by an optical density analysis using Un-Scan-It Version 5.1 (Silk Scientific, Orem, Utah).

Statistical Analyses

Data are presented as group means±S.E.M. Statistically significant differences were determined by a one-way analysis of variance followed by a Student-Newman-Keuls post hoc analysis.

Results

The PhytoSERMs tested are shown in FIG. 1.

Selective Binding for both ERβ and ERα

Figure 3A:
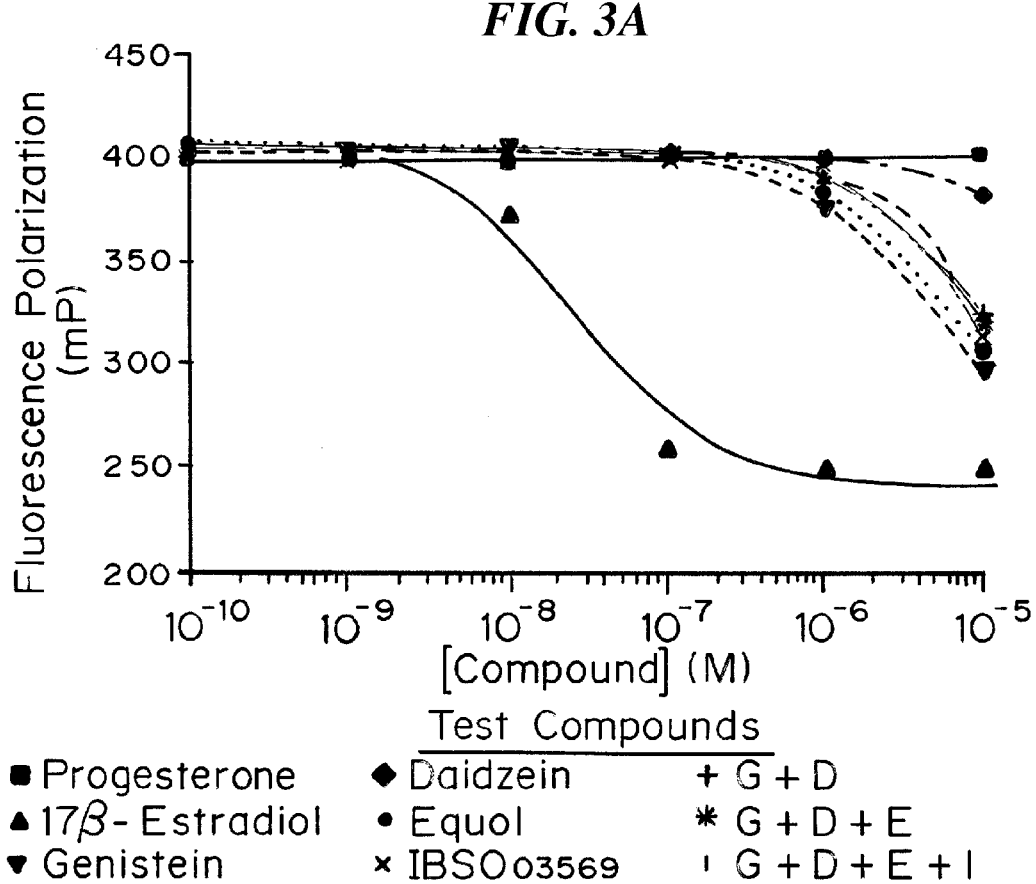
FIGS. 3A and 3B show the competition binding curves for ERα (FIG. 3A) and ERβ (FIG. 3B) (molar concentration versus fluorescence polarization (mP)) of progesterone (■), 17β-estradiol (▲), genistein (G, ▼), daidzein (D, ♦), equol (E, ●), IBSO03569 (I, X), G+D (+), G+D+E (*), and G+D+E+I (|).
Figure 3B:
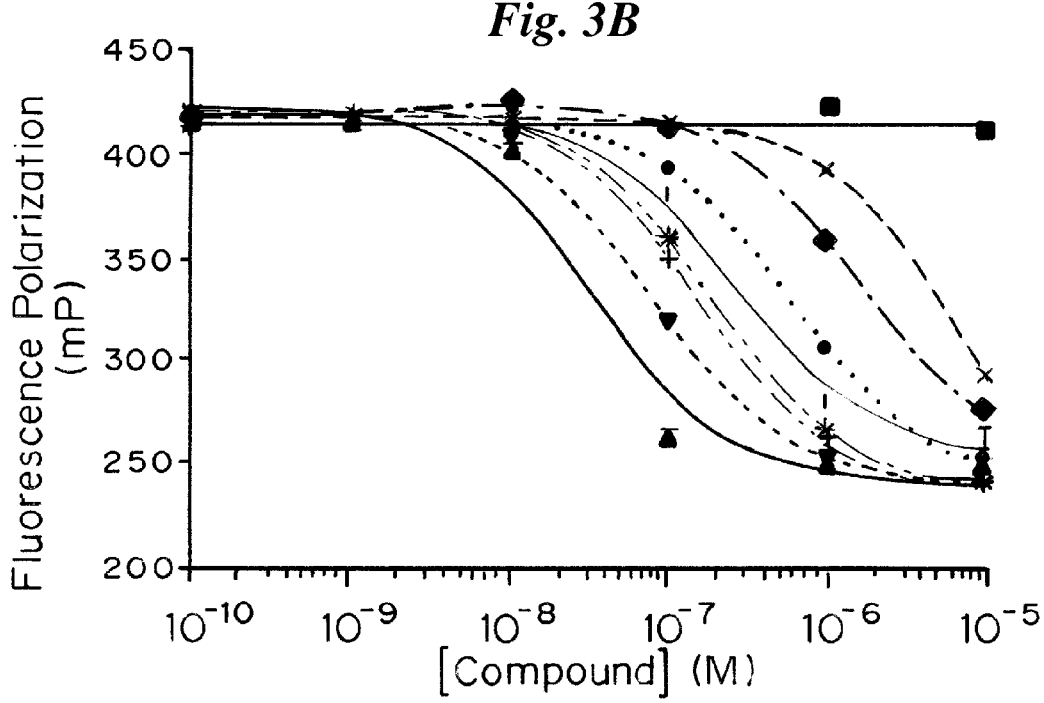

FIGS. 3A and 3B presents the competition binding curves of four known ER ligands for both ERβ and ERα. The $IC_{50}$ determined for these ligands from the binding curves are consistent with the previously reported values using alternative methods such as radioligand assay, demonstrating the reliability of this assay in determining the binding profiles of small molecules to both ERs.

FIGS. 3A and 3B show the competition binding curves for ERα and ERβ. Data were generated with a fluorescence polarization-based competitive binding assay using full-length human ERα and ERβ, and plotted against the logarithm of serially diluted concentrations of the test compounds (or combinations). Progesterone served as a negative control. 17 β-Estradiol served as a positive control. Combined formulations were composed of equivalent molar of individual phytoSERMs included. G: genistein; D: daidzein; E: equol; I: IBSO03569. 17β-estradiol has no binding preference to ERα or to ERβ. The concentration of a test molecule resulting in the half-maximum shift in polarization value equals its $IC_{50}$. Non-convergence within the dose range, predicts that either the molecule does not bind to the receptor or that the binding affinity is very low. Data derived from the binding curves are summarized in Table 2.

TABLE 2

Binding data for ERα and ERβ

| Compounds | ERα | | | ERβ | | | |
|---|---|---|---|---|---|---|---|
| Progesterone | $IC_{50}$ (μM) | RBA (%)[A] | $R^{2B}$ | $IC_{50}$ (μM) | RBA (%)[A] | $R^{2B}$ | Selectivity (β/α) |
| | Non-Binding | | | Non-Binding | | | |
| 17β-Estradiol | 0.0253 | 100.0 | 0.9791 | 0.0325 | 100.00 | 0.9611 | 0.78 |
| Genistein | 4.735 | 0.5343 | 0.9811 | 0.0789 | 41.12 | 0.9908 | 60.0 |
| Daidzein | 26.65 | 0.0949 | 0.7876 | 1.738 | 1.867 | 0.9883 | 14.27 |
| Equol | 5.876 | 0.4306 | 0.9948 | 0.5825 | 5.571 | 0.9986 | 10.09 |
| IBSO03569 | 1695 | 0.0015 | 0.9917 | 7.819 | 0.415 | 0.9959 | >100 |
| G + D | 9.896 | 0.2557 | 0.9865 | 0.1574 | 20.62 | 0.9970 | 62.87 |
| G + D + E | 15.71 | 0.1610 | 0.9925 | 0.1902 | 17.06 | 0.9969 | 82.60 |
| G + D + E + I | 15.85 | 0.1596 | 0.9932 | 0.2615 | 12.41 | 0.9891 | 60.61 |

[A]RBA (%) refers to the relative binding affinity of the test compound (combination) that is expressed as the percent of the binding affinity of 17 β-estradiol (RBA = 100%).
[B]$R^2$ refers to goodness of fit of nonlinear regression between the binding curve and the data. Between 0.0 and 1.0, higher values indicate that the curve fits the data better. A fit with a R2 at 1.0 indicates that all points lie exactly on the curve with no scatter.

IC50, determined from the binding curve by a nonlinear least-squares analysis, refers to the concentration of the test phytoestrogen that displaces half of EL Red from the ER. Relative binding affinity (RBA), expressed as the percent of the binding affinity of 17β-estradiol (RBA 100%), indicates the relative binding ability of the test phytoestrogen as compared to 17β-estradiol. R2 reflects the goodness of the fit of nonlinear regression between the binding curve and data. R2 ranges between 0.0 and 1.0. A R2 of 1.0 indicates that all points lie exactly on the curve with no scatter. The reliability of this assay in determining the binding profile of ligands to both ERs has been validated in our previous analyses. The IC50 of 17β-estradiol, 25.3 nM for ERα ($R2=0.98$) and 32.5 nM for ERβ ($R2=0.96$), were consistent with the values reported in the literature. As expected, the negative control molecule, progesterone, did not bind to either ER. Among four test phytoestrogens, genistein exhibited the maximal binding to both ERα (IC50=4.74 μM; $R2=0.98$) and ERβ (IC50=78.9 nM; $R2=0.99$), with an approximately 60-fold binding preference for ERβ over ERα. The binding affinity of genistein to ERβ was approximately 41% of the value from 17β-estradiol. In comparison with genistein, the binding affinities of daidzein to both ERα (IC50=26.7 μM; $R2=0.79$) and ERβ (IC50=1.74 μM; $R2=0.99$) were weaker but maintained an approximately 14-fold binding preference for ERβ. Equol exhibited a similar binding affinity to genistein for ERα (IC50=5.88 μM; $R2=0.99$), but with a less, approximately 10-fold, binding preference to ERβ (IC50=0.58 μM; $R2=1.00$). Although IBSO03569 exhibited the greatest binding selectivity toward ERβ (>100-fold), the binding affinity was the lowest, with an IC50 at 1695 μM for ERα ($R2=0.99$) and 7.82 μM for ERβ ($R2=1.00$). The combination of genistein and daidzein (G+D) exhibited a decreased binding affinity compared to genistein alone, with IC50 values (IC50=9.90 μM for ERα; $R2=0.99$; IC50=0.16 μM for ERβ; $R2=1.00$) approximately 50% of genistein alone. However, the binding selectivity of G+D was slightly higher, with an approximately 63-fold binding preference for ERβ. The combination of genistein, daidzein and equol (G+D+E) exhibited a greater decrease in the binding affinity toward ERα (IC50=15.7 μM; $R2=0.99$) than the decrease toward ERβ ($IC_{50=0.19}$ μM; $R2=1.00$), which was slightly lower than the value from G+D. However, G+D+E exhibited a much improved, approximately 83-fold, binding preference for ERβ, which represents an approximate 30% increase compared with genistein alone or G+D. The combination of genistein, daidzein, equol and IBSO03569 (G+D+E+I) exhibited a similar binding affinity to G+D+E toward ERα ($IC_{50=15.9}$ μM; $R2=0.99$), but with a lower, approximately 61-fold, binding preference for ERβ (IC50=0.26 μM; $R2=0.99$), which is similar to the binding selectivity from the combination of G+D.

Neuroprotective Effect

Neuroprotective efficacy of test phytoestrogens, when administered alone or in combination, was evaluated in rat primary hippocampal neuronal cultures challenged with neurotoxic glutamate or β-amyloid1-42(Aβ1-42). A dose-response analysis was first conducted to determine the concentration for each test phytoestrogen resulting in the maximal neuronal survival following an acute exposure to a supraphysiological concentration of glutamate. Neuronal cultures grown for 7 d in vitro (DIV) were pretreated with test phytoestrogens at serially diluted concentrations (1 nM to 10 μM) for 48 h, followed by a 5-min exposure to 100 μM glutamate. Neuronal viability was assessed by the lactate dehydrogenase (LDH) release in the culture medium measured 24 hr later, which served as a indicator of neuronal membrane integrity, a minimum criteria for neuroprotection.

Table 3 and FIG. 4 A-D show the dose-dependent neuroprotective effects of four ERβ-selective phytoSERMs against supraphysiological glutamate (100 μM)-induced neurotoxicity in primary hippocampal neurons by measurement of LDH release.

TABLE 3

Dose-dependent effects of individual phytoSERMs against glutamate-induced neurotoxicity in primary hippocampal neurons by LDH measurements[A]

| | LDH Release (% of Control) |
|---|---|
| Treatment__Genistein | |
| Control | 100.00 ± 3.09 |
| Glutamate alone | 410.99 ± 8.27[##] |
| 1 nM | 361.03 ± 7.71** |
| 10 nM | 350.02 ± 8.21** |
| 100 nM | 347.24 ± 16.96** |
| 1 μM | 356.79 ± 11.15** |
| 10 μM | 377.84 ± 8.45** |
| Treatment__Daidzein | |
| Control | 100.00 ± 4.28 |
| Glutamate alone | 378.26 ± 11.95[##] |
| 1 nM | 338.39 ± 16.49 |
| 10 nM | 333.98 ± 9.10* |
| 100 nM | 301.42 ± 7.70** |
| 1 μM | 318.49 ± 15.92** |
| 10 μM | 325.41 ± 26.12* |
| Treatment__Equol | |
| Control | 100.00 ± 14.95 |
| Glutamate alone | 460.27 ± 12.20[##] |
| 1 nM | 453.50 ± 23.37 |
| 10 nM | 403.78 ± 17.02* |
| 100 nM | 331.59 ± 9.67** |
| 1 μM | 381.80 ± 12.01** |
| 10 μM | 390.21 ± 9.40** |
| Treatment__IBSO03569 | |
| Control | 100.00 ± 2.05 |
| Glutamate alone | 281.17 ± 6.77[##] |
| 1 nM | 262.41 ± 10.60 |
| 10 nM | 270.86 ± 12.94 |
| 100 nM | 220.56 ± 6.80** |
| 1 μM | 246.30 ± 7.70** |
| 10 μM | 307.53 ± 2.62 |

[A]Primary hippocampal neurons grown for 7 DIV were pretreated with the test phytoSERMs at serially diluted concentrations for 48 h, followed by a 5-min exposure to 100 mM glutamate. The amount of LDH released into the culture media was measured 24 h later.
[B]Data are derived from a single experiment and are representative of at lease three independent experiments. Results are presented as the percent of LDH release from vehicletreated control cultures and expressed as means ± S.E.M., n 6.
[##]$P < 0.01$ compared to vehicle-treated control cultures,
*$P < 0.05$ and
**$P < 0.01$ compared to glutamate alone-treated cultures.

Data summarized in Table 3 and FIGS. 4A-D demonstrated that cultures exposed to glutamate alone had significantly increased LDH release in the medium as compared to vehicle-treated control cultures (## $P<0.01$), although the relative amount of release varied across cultures. All four test phytoestrogens induced a concentration-dependent and moderate reduction of the LDH release as compared to glutamate alone-treated cultures (* $P<005$ and ** $P<0.01$). A maximal reduction occurred at 100 nM, exhibiting significant differences from neuronal responses induced by some of the neighboring concentrations (φ$P<0.05$ and φφ $P<0.01$, $P<0.05$ and ζζ $P<0.01$, f $P<0.05$ and ff $P<0.01$, compared with cultures treated with 10 nM, 1 μM and 10 μM phytoestrogens, respectively).

Figure 4A:
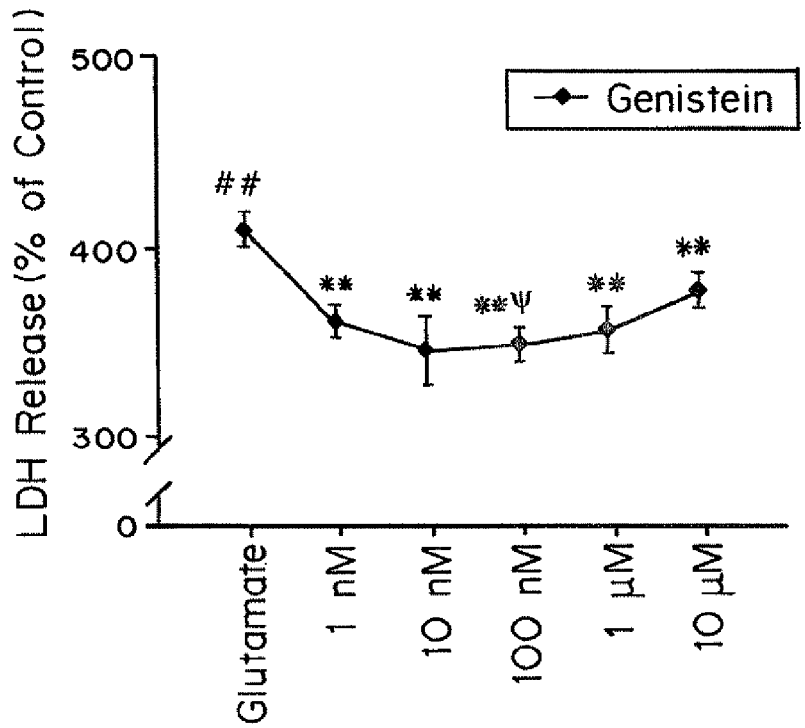
FIGS. 4A-D are graphs showing the neuronal viability as a function of phytoserm (genistein (Figure A), daidzein (Figure B), equol (Figure C), and IBSO03569 (Figure D)) concentration as assessed by lactate dehydrogenase (LDG) release as an indicator of neuronal membrane integrity in the culture medium 24 hours after exposure to supraphysiological glutamate (100 μm) in rat primary hippocampal neurons.
Figure 4B:
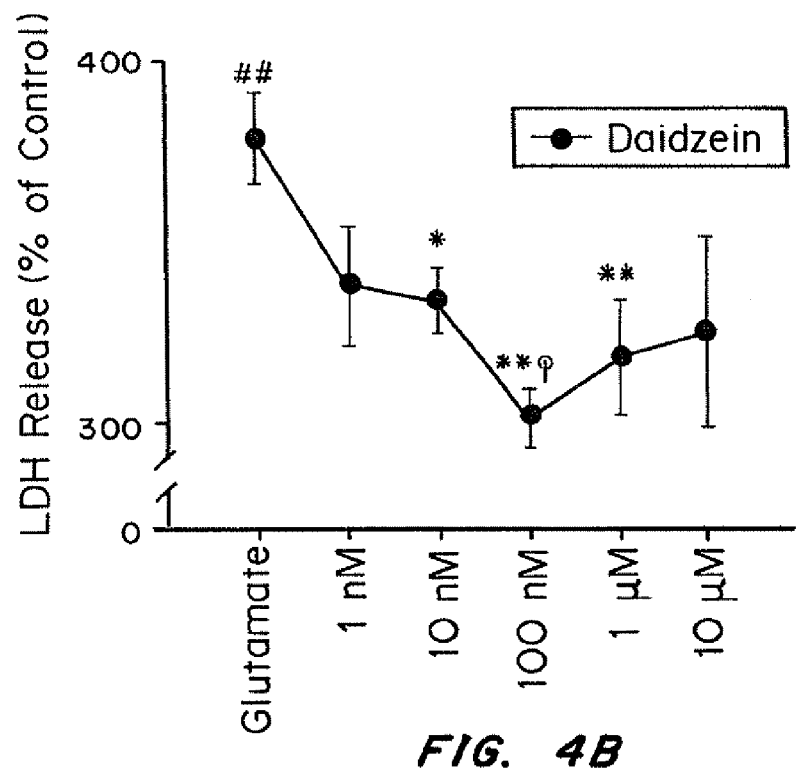
Figure 4C:
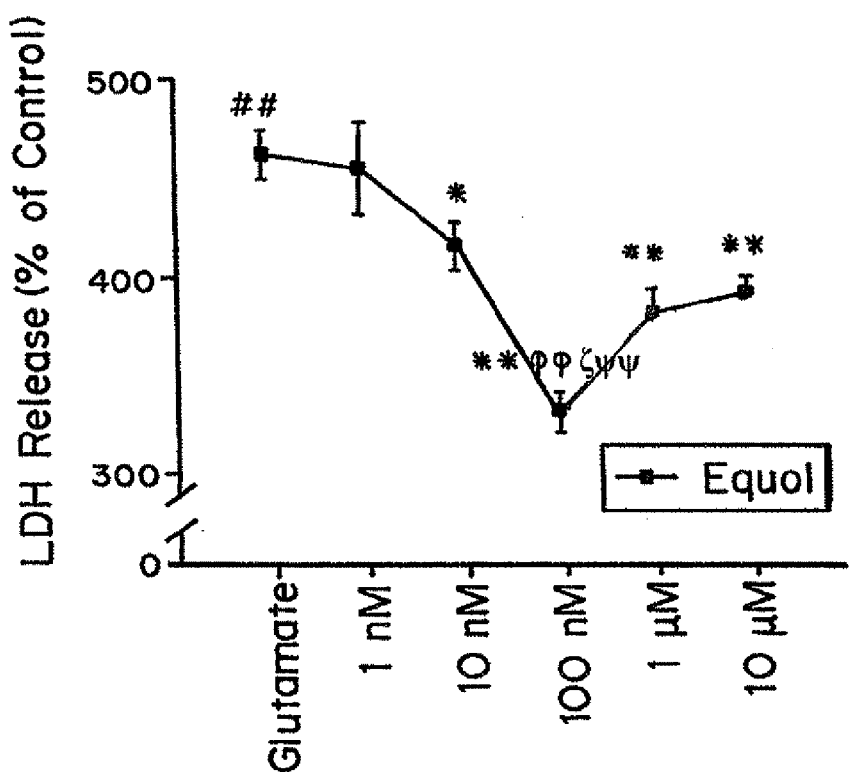
Figure 4D:
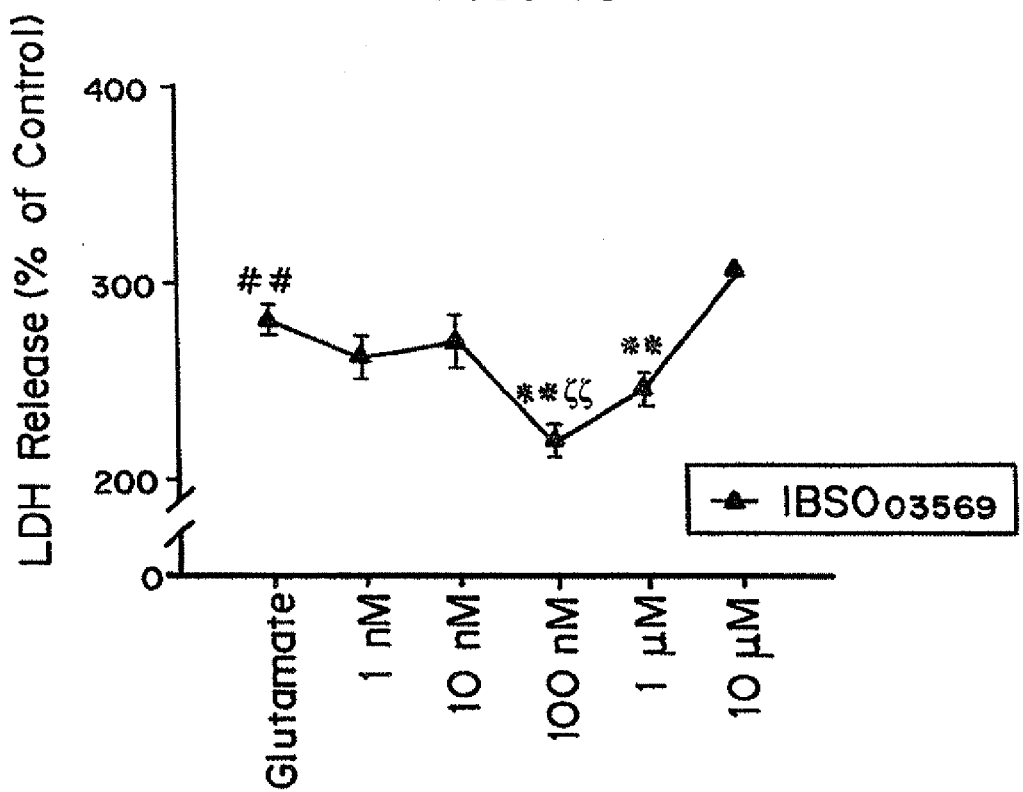
Figure 4E:
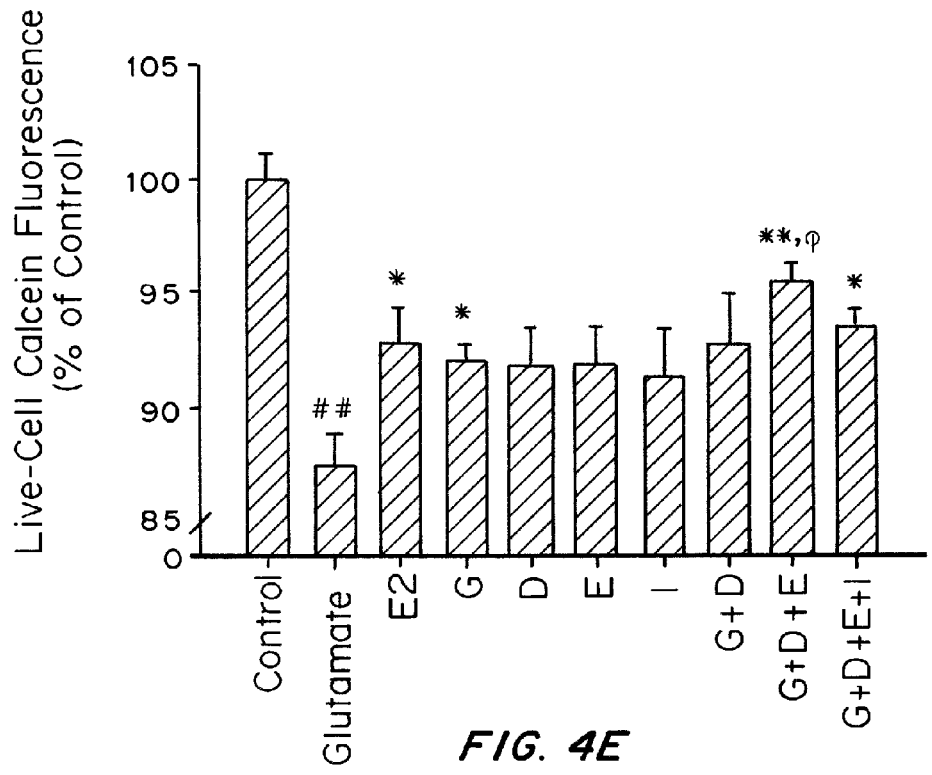
FIG. 4E is a graph showing the neuronal viability as assessed by calcein AM staining as an indicator of neuronal metabolic activity for phytoSERMs when administered alone at concentrations that elicited the maximal neuroprotective effects as revealed from the dose-response analyses (100 nM for all four molecules): G, D, E and I, or co-administered: G+D, G+D+E, and G+D+E+I, against 100 μM glutamate in rat primary hippocampal neurons.
Figure 4F:
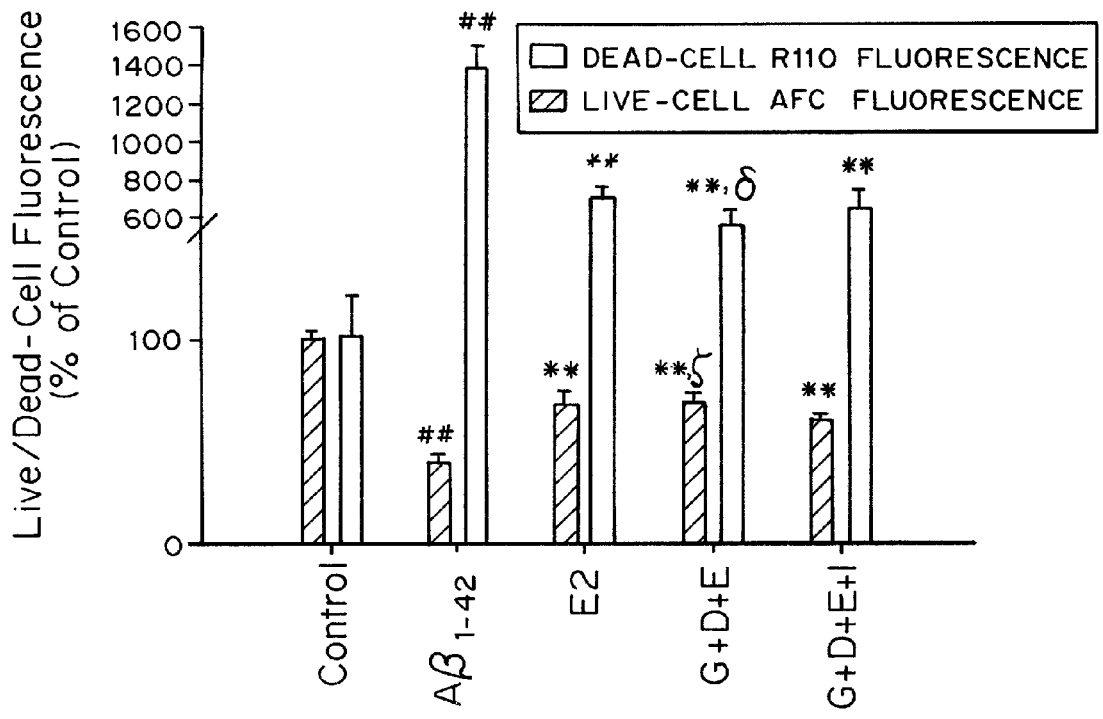
FIG. 4F is a graph showing the neuronal viability as assessed by a dual-measurement of live cell AFC and dead-cell R110 staining as indicators of neuronal metabolic activity and membrane integrity, respectively, for G+D+E and G+D+E+I. 17β-estradiol (E2) was used as a positive control.

Data summarized in FIG. 4E were derived from further analyses conducted to determine whether the test phytoestrogens administered at the EC100 of 100 nM against glutamate-induced damage in neuronal membrane integrity would be effective in protecting neurons against glutamate-induced deficits in metabolic activity, and whether combined use of select phytoestrogens would increase neuroprotective efficacy as compared to when administered alone. Hippocampal neuronal cultures grown for 7 DIV were pretreated with 17β-estradiol (10 nM), individual phytoestrogens, genistein (G, 100 nM), daidzein (D, 100 nM), equol (E, 100 nM) and IBSO03569 (I, 100 nM), the combination of G (100 nM) and D (100 nM), G (100 nM), D (100 nM) and E (100 nM), or G (100 nM), D (100 nM), E (100 nM) and I (100 nM), for 48 h, followed by a 5-min exposure to 100 μM glutamate. Neuronal viability was assessed by the live-cell calcein AM staining measured 24 hr later, which served as an indicator of neuronal metabolic activity (44). Data shown in FIG. 4E demonstrated that an acute exposure to 100 nM glutamate was not only deleterious to the neuronal membrane integrity as previously determined, but also toxic to neuronal metabolic viability as indicated by the significantly reduced live-cell calcein staining as compared to vehicle-treated control cultures (## $P<0.01$). Cultures treated with 17β-estradiol exhibited a significantly increased viability as evidenced by an average of 43.0% (±12.6%) increase in live-cell calcein fluorescence as compared to glutamate alone treated cultures (* $P<0.05$). Among four phytoestrogens administered alone, only genistein induced a significant increase in neuronal viability, with an average of 36.4% (±7.2%) increase in calcein fluorescence as compared to glutamate alone-treated cultures (*$P<0.05$). Although the other three phytoestrogens, daidzein, equol and IBSO03569, when administered at 100 nM, were protective at the level of neuronal membrane integrity, they were insufficient to induce a statistically significant effect at the level of neuronal metabolic activity. In comparison, combined use of select phytoestrogens exerted an increased neuroprotective efficacy. The combination of G+D induced an average of 42.5% (±17.8%) increase in neuronal viability, which however was not statistically significant. The combination of G+D+E induced a maximal neuronal survival against glutamate-induced toxic insult (64.8%±5.6% increase compared with glutamate alone-treated cultures, **$P<0.01$), which was significantly greater than the effect induced by 17β-estradiol (φ$P<0.05$). The combination of G+D+E+I induced an average of 48.5% (±6.8%) increase in neuronal viability as compared to glutamate alone-treated cultures (*$P<0.05$).

Based on the significant neuroprotective activity exhibited by combinations of G+D+E and G+D+E+I, subsequent experiments were conducted to determine the impact of these combined formulations on neuronal survival when challenged with an extended exposure to an aggregated form of Aβ1-42. Primary hippocampal neuronal cultures grown for 7 DIV were pretreated with either 17β-estradiol, the combination of G+D+E or G+D+E+I for 48 h, followed by a 2-d exposure to 3.0 μM Aβ1-42 aggregated prior to the treatment. Neuronal viability was assessed by a dual measurement of live-cell AFC and dead-cell R110 staining, as indicators of neuronal metabolic activity and membrane integrity, respectively. Data shown in FIG. 4F demonstrated that a 2-d exposure to Aβ$_{1-42}$ was significantly neurotoxic as evidenced by a reduced AFC and increased R110 staining as compared to vehicle-treated control cultures (## $P<0.01$). Treatment with 17β-estradiol induced a significant increase in neuronal survival against Aβ$_1$-42 as indicated by both measurements (45.4%±10.3% and 54.1%±1.9% increase in neuronal viability measured by AFC and R110 staining, respectively;  $P<0.01$). Consistent with the data against glutamate, the combination of G+D+E exerted the greatest neuro-protective activity on both neuronal metabolic viability (47.6%±6.1% increase relative to Aβ$_{1-42}$ alone-treated cultures,  $P<0.01$; ξ $P<0.05$ compared with G+D+E+I treated cultures) and membrane integrity (65.8%±2.3% increase compared with Aβ$_{1-42}$ alone-treated cultures,  $P<0.01$; δ $P<0.05$ compared with 17β-estradiol-treated cultures). The combination of G+D+E+I induced an average of 32.2% (±2.3%) increase in neuronal viability measured by AFC staining and 58.0% (±2.7%) increase measured by R110 staining, both of which were statistically significant relative to Aβ1-42 alone-treated cultures ( $P<0.01$).

Together, the combination of G+D+E was found to be most neuroprotective, followed by the combination of G+D+E+I, based on measurements of both neuronal membrane integrity and metabolic activity when neurons were challenged with either an acute exposure to a supraphysiological concentration of glutamate or an extended exposure to an aggregated form of Aβ$_{1-42}$, both of which were sufficient to induce a significant neurotoxicity at the time when neuronal viability was measured. To determine whether the in vitro findings were predictive of in vivo efficacy, ovariectomized adult female rats (14-16 weeks of age) were treated once daily for 2 d with a subcutaneous injection of vehicle (control), 17β-estradiol (70 ug/kg BW), or phytoestrogen formulations: genistein alone or the combination of G+D+E or G+D+E+I at 6 mg/kg BW. The dosage of 17β-estradiol was designed to be commensurate with a commonly used dose (0.625 mg/d) reported in epidemiological and clinical studies. The dosage of phytoestrogen formulations was commensurate with 50 mg/d exposure in humans based on an estimated amount of total isoflavone intake in Asian populations. Following a 2-d treatment, animals were sacrificed and brain tissues were evaluated for 1) mitochondrial bioenergetic efficiency; 2) mitochondrial anti-apoptotic protein expression; 3) Aβ-degrading enzyme protein expression. Uteri were excised at the time of sacrifice, and both a wet and dry weight was measured to evaluate the impact of treatments on uterine growth.

Expression of Anti-Apoptotic Proteins Bcl-2 and Bcl-xL

Figure 5:
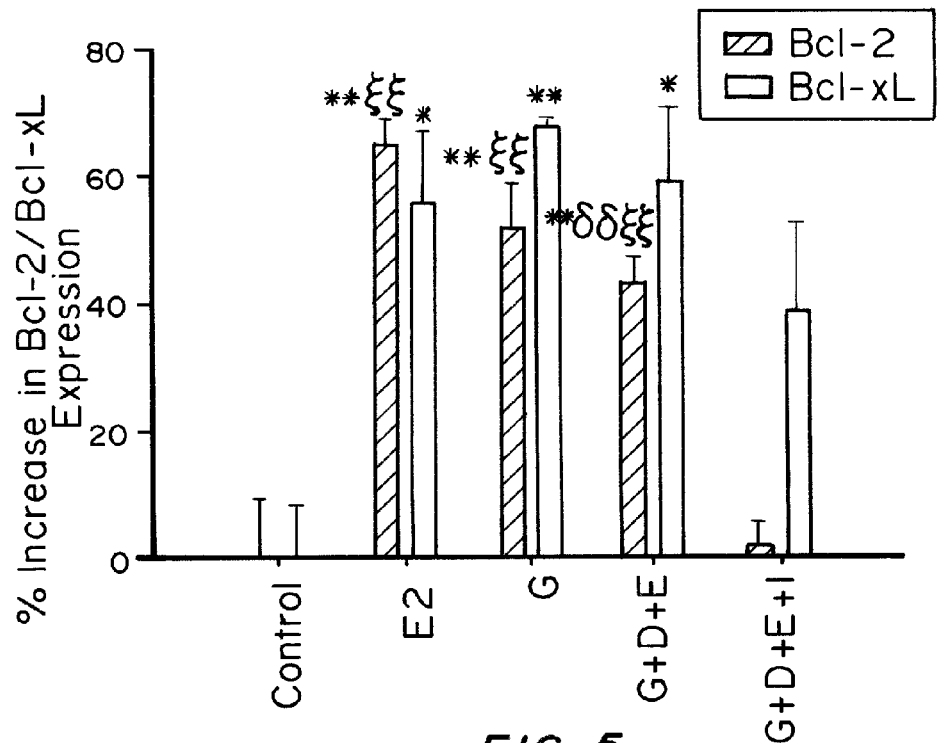
FIG. 5 is a graph showing the effects of G, G+D+E, and G+D+E+I on the expression of the anti-apoptotic proteins, Bcl-2 and Bcl-xL, in hippocampal tissues derived from ovariectomized adult female rats. 17β-estradiol (E2) was used as a positive control.

FIG. 5 shows the effects on Bcl-2 and Bcl-XL expression in hippocampal tissues derived from adult ovariectomized rats. Adult ovariectomized rats were given, once daily, 2 subcutaneous injections of the test compounds (or combinations). Rats were sacrificed 24 h later following the 2nd injection. Hippocampal tissues were homogenized followed by Western blot analyses. Combined formulations were composed of equivalent molar in (A) and equivalent weight in (B) of individual phytoSERMs including G: genistein; D: daidzein; E: equal; and I: IBSO03569.

17β-estradiol (70 μg/kg/d for 2 d) induced a significant upregulation of both Bcl-2 (64.8±4.0% increase compared to vehicle-treated control animals, ** $P<0.01$) and Bcl-xL expression (55.2±11.2% increase compared to vehicle-treated control animals, * $P<0.05$) in the female rat hippocampus (FIG. 5). Genistein alone (6 mg/kg/d) induced a magnitude of expression comparable to 17β-estradiol-treated animals, of both Bcl-2, with an average increase of 51.9% (±6.2%;  $P<0.01$), and Bcl-xL, with an average increase of 67.8 (±0.7%;  $P<0.01$), compared to vehicle-treated control animals (FIG. 5). Increased Bcl-2 expression (43.2±4.1% increase compared to vehicle-treated control animals, * $P<0.05$) induced by the combination of G+D+E (6 mg/kg/d), was significantly lower than that induced by 17β-estradiol (δδ $P<0.01$). There was a greater variance in the Bcl-xL expression in G+D+E-treated animals, with an average increase of 58.9% (±11.7%) compared to vehicle-treated control animals (* $P<0.05$). Animals treated with G+D+E+I (6 mg/kg/d, 2d) did not exhibit a significant change in either protein, although there was an average increase of 38.6% (±11.7%) in BclxL expression, which was not statistically significant due to the large variance among animals. Bcl-2 expression (1.5±4.0% increase compared to vehicle-treated control animals) induced by G+D+E+I was significantly lower than all other treatment groups (ξξ $P<0.01$).

Up-regulation of the Bcl-2 family anti-apoptotic proteins have been associated with the neuroprotective mechanism elicited by E2. These data indicate that a combined used of multiple ERβ-selective phytoestrogens is effective to activate the neuroprotective mechanism leading to improved neuronal survival against neurodegenerative insults.

Estrogen receptor interaction with p85/PI3K also enhances pAkt, which phosphorylates the proapoptotic protein Bcl-2-associated death protein (BAD) to prevent heterodimerization with, and inactivation of, Bcl-2. In cortical neurons, estradiol induced pAkt translocation to the nucleus. Recent analyses indicate that estradiol, via the PI3K signaling pathway, activates both the Akt and the ERK1/2 cascades in the same population of cortical and hippocampal neurons. Simultaneous activation of two pathways that prevent mitochondria from activating cell-death cascades is likely to promote neuron survival.

Increased Expression of the anti-β-Amyloid Protein (IDE) and Neprilysin (NEP)

Figure 6:
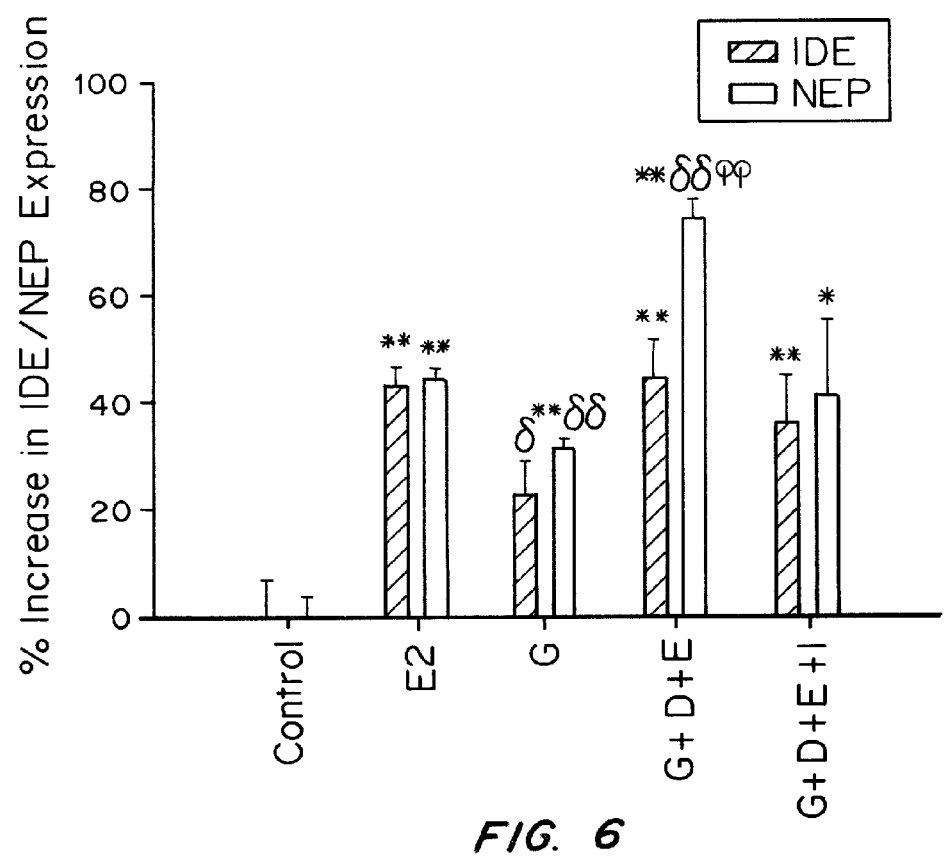
FIG. 6 is a graph showing the effects of G, G+D+E, and G+D+E+I on the expression of β-amyloid-degrading proteins, insulin-degrading enzyme (IDE) and neprilysin (NEP), in hippocampal tissues derived from ovariectomized adult female rats. 17β-estradiol (E2) was used as a positive control.

A major neuropathological hallmark of AD is the significant deposition of Aβ peptide which can lead to formation of Aβ plaques. Clinical investigations have revealed a strong link between a decrease in expression and activity of Aβ-degrading enzymes and AD pathogenesis. Several Aβ-degrading enzymes have been identified, including insulin-degrading enzyme (IDE) and neprilysin (NEP), which appear to play a more significant role than others in regulating Aβ catabolic clearance in the brain. Results shown in FIG. 6 from Western blot analyses of the same hippocampal protein samples used for the Bcl-2/Bcl-xL analyses demonstrated that all treatment groups exhibited an enhanced expression of both IDE and NEP. Specifically, animals treated with 17β-estradiol (70 µg/kg/d for 2 d) exhibited an average increase of 42.4% (±3.9%) in IDE and a 44.0% (A: 1.8%) increase in NEP expression, both of which were statistically significant as compared to vehicle-treated control animals (** P<0.01).

Among three groups treated with different phytoestrogen formulations, the combination of G+D+E (6 mg/kg/d, 2d) induced a magnitude of upregulation of IDE similar to 17β-eastradiol (44.1%±7.2% increase compared with vehicle-treated control animals, ** P<0.01). In comparison, genistein alone (6 mg/kg/d, 2d) induced an average increase of 21.6% (±3.9%) as compared to vehicle-treated control animals, which was not statistically significant (δ P<0.05 compared with 17β-estradiol-treated animals). The combination of G+D+E+I (6 mg/kg/d, 2d) induced a slightly lower magnitude of change in IDE expression (35.6%±8.4% increase compared with vehicle-treated control animals, * P<0.05) than that induced by G+D+E. For induction of the NEP protein expression, the combination of G+D+E induced a maximal effect among all treatment groups, with an average increase of 73.8% (±3.4%)( P<0.01 compared with vehicle-treated control animals), which was statistically greater than that induced by either 17β-estradiol (δδ P<0.01) or genistein alone (φφ P<0.01). Although genistein alone induced a significant increase in NEP protein expression (31.2%±1.2% increase compared with vehicle-treated control animals,  P<0.01), the magnitude of induction was lower than that induced by G+D+E or 17β-estradiol (δδ P<0.01). Animals treated with G+D+E+I had a greater variance and exhibited an average increase of 40.4% (±14.4%) in NEP expression relative to vehicle-treated control animals (* P<0.05).

It is clear that one neuropathological hallmark of AD is a significant deposition of extracellular Aβ peptide, as referred to Aβ plaque. Impaired Aβ clearance and/or degradation has been demonstrated to contribute in part to Aβ plaque formation in AD brain. Besides degrading insulin and several regulatory peptides, IDE, a metalloprotease enzyme, has been demonstrated to play a key role in degrading AP peptide monomer in the brain. Choronic upregulation of IDE represents an efficacious therapeutic approach to lowering the steady-state Aβ level in the brain and eventually preventing the occurrence of Alzheimer-type pathology. Therefore, these data indicate that coadministration of multiple ERβ-selective phytoestrogens have the potential to activate the anti-Aβ mechanism, and as a result, maintain the brain in a long-term healthy status.

Effect on Forebrain Mitochondria

Mitochondrial dysfunction resulting from molecular defects in oxidative phosphorylation has been implicated in a variety of neurodegenerative diseases, including AD and Parkinson's. Development of AD pathology is accompanied by a decrease in mitochondrial respiration, in part due to a decrease in expression and activity of cytochrome c oxidase (COX) and other enzymes that play an essential role in mitochondrial electron transport chain (ETC). Mitoenergetic deficits compromise ATP generation and accelerate the accumulation of free radicals, which could cause or exacerbate neuronal degeneration. A recent proteomic profiling of brain-derived mitochondria from animals treated with 17β-estradiol identified a number of proteins upregulated by the treatment, of them, the majority are involved in regulation of cellular energetics represented by the tricarboxylic acid cycle and ETC. It is hypothesized that such an enhanced mitoenergetic state induced by 17β-estradiol acts as a proactive buffer against mitochondrial functional decline associated with menopause and aging. In this experiment, the impact of ERβ-selective phytoestrogenic formulations on brain mitoenergetics was assessed in ovariectomized adult female rats (FIGS. 7 and 8). Following a 2-week recovery period from ovariectomy, animals were treated once daily for 2 d with a subcutaneous injection of 17β-estradiol (70 µg/kg/d for 2 d) or phytoestrogen formulations (6 mg/kg/d for 2 d). Forebrain mitochondria were isolated and purified at time of sacrifice. Analysis of the purity of mitochondria is provided in our previous report. Determination of the respiratory activity was immediately conducted, which served as a primary marker of mitochondrial efficiency. COX activity was subsequently determined as a secondary marker of mitochondrial efficiency.

Figure 7A:
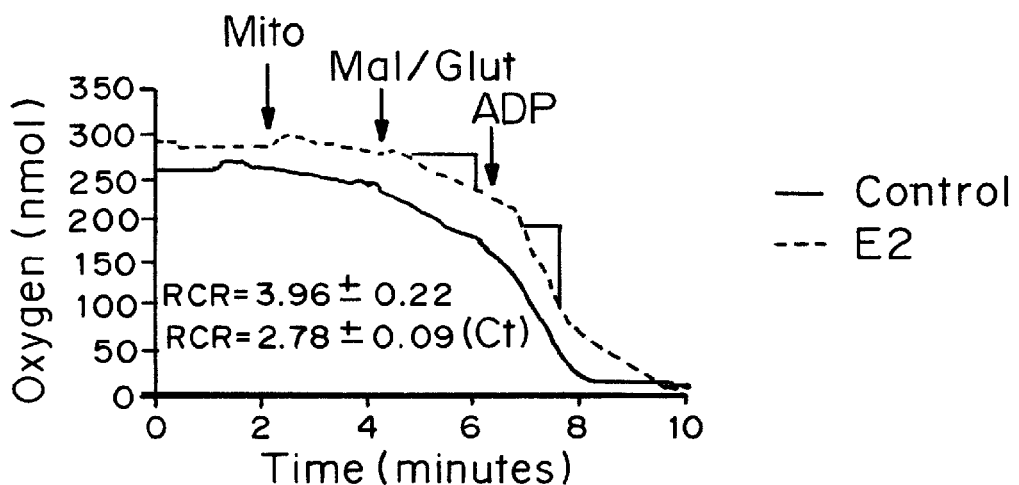
FIGS. 7A-7E are graphs showing the effects of G (FIG. 7B), G+D+E (FIG. 7C), and G+D+E+I (FIG. 7D) on forebrain mitochondrial respiratory activity in ovariectomized adult female rats. 17β-estradiol (E2) was used as a positive control (FIG. 7A).
Figure 7B:
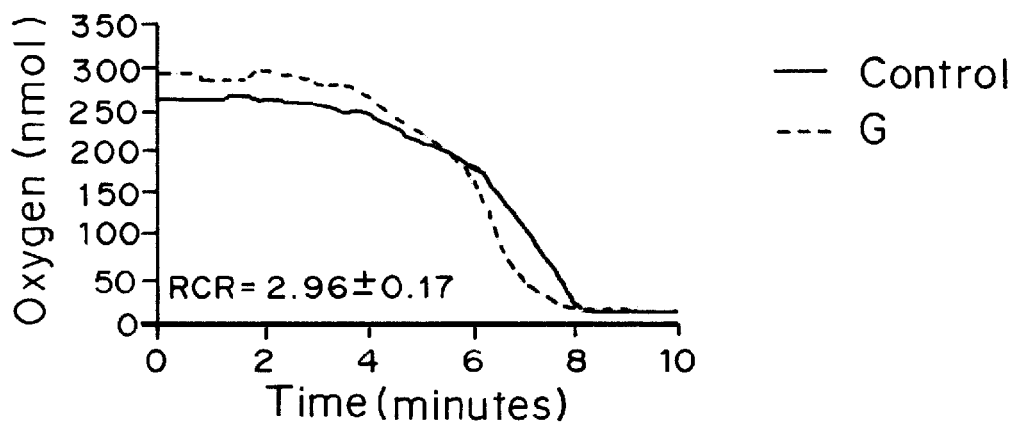
Figure 7C:
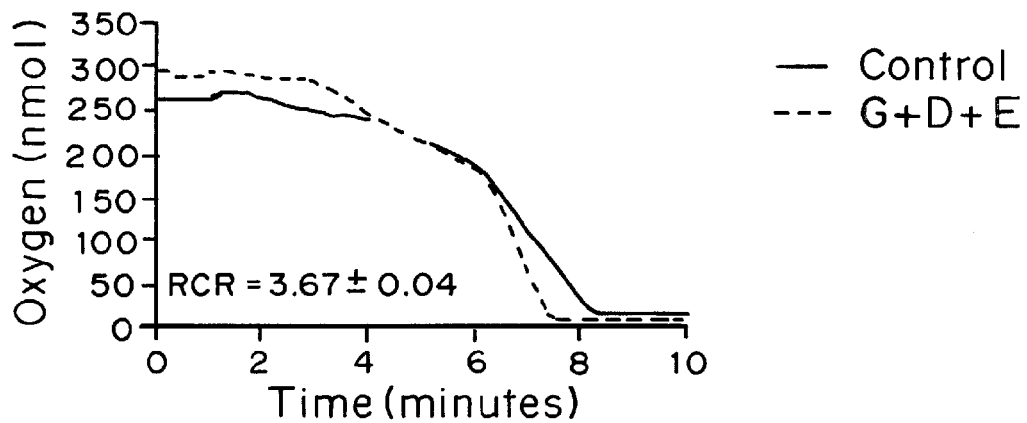
Figure 7D:
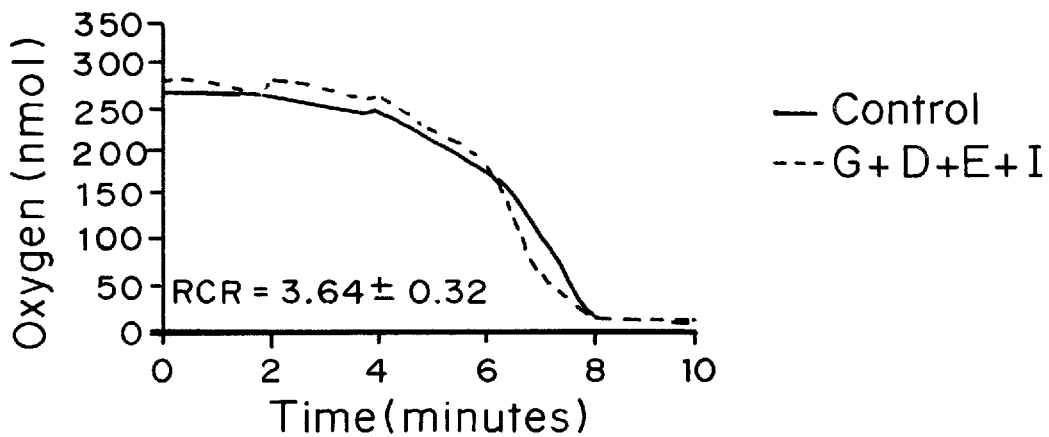
Figure 7E:
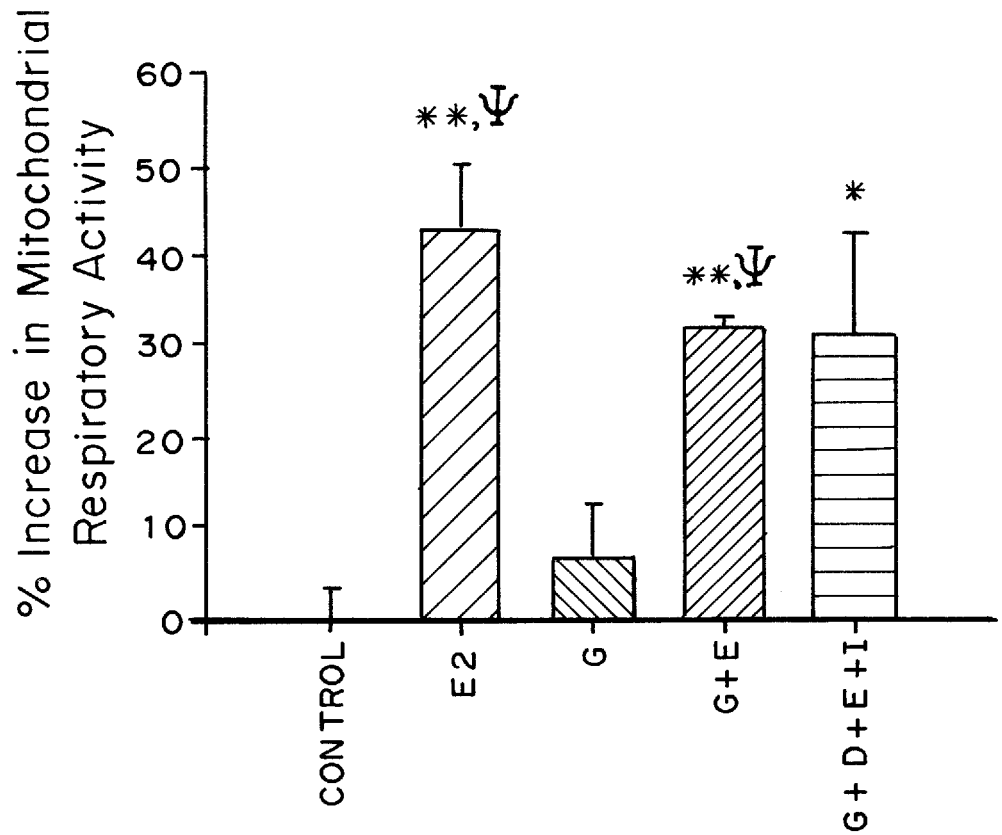
Figure 8A:
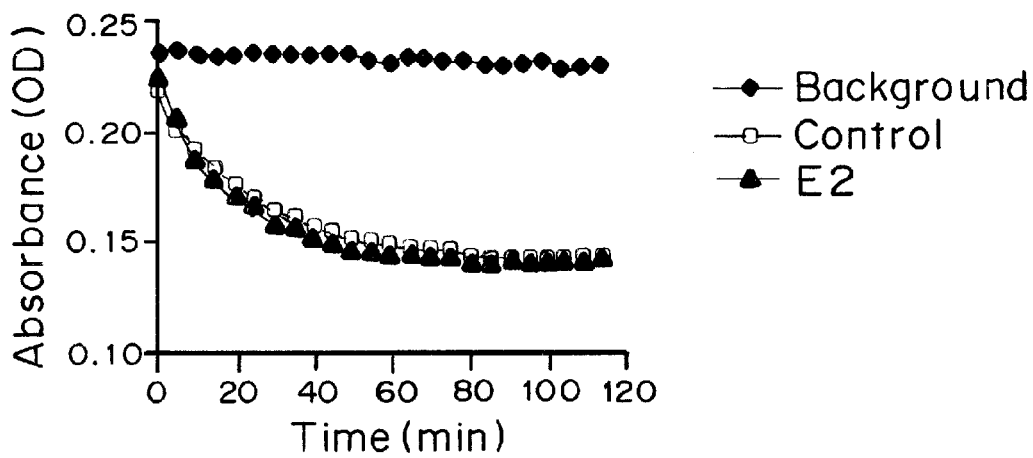
FIGS. 8A-8E are graphs showing the effects of G (FIG. 8B), G+D+E (FIG. 8C), and G+D+E+I (FIG. 8D) on forebrain mitochondrial cytochrome c oxidase (COX) activity in ovariectomized adult female rats. 17β-estradiol (E2) was used as a positive control (FIG. 5A).
Figure 8B:
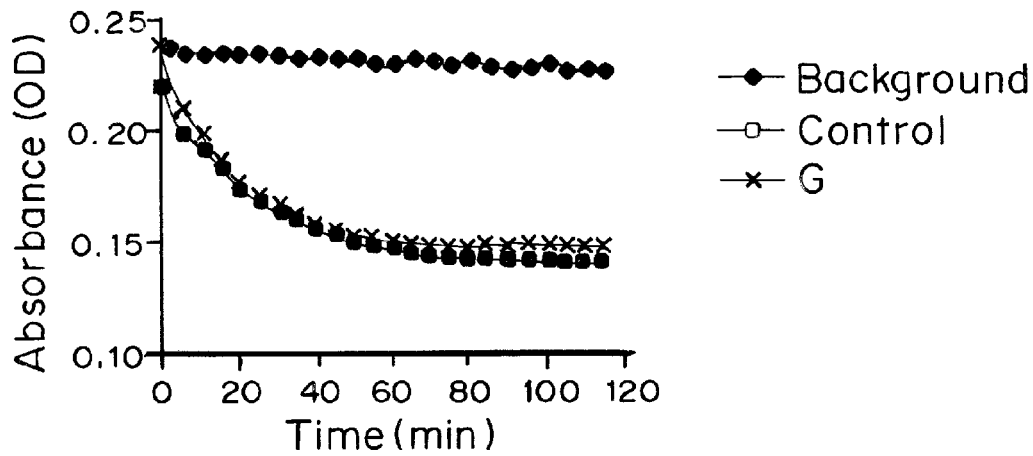
Figure 8C:
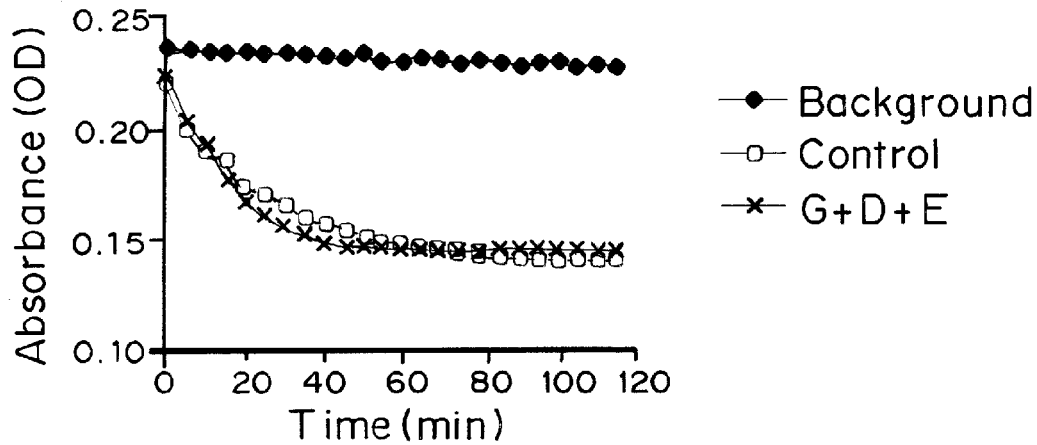
Figure 8D:
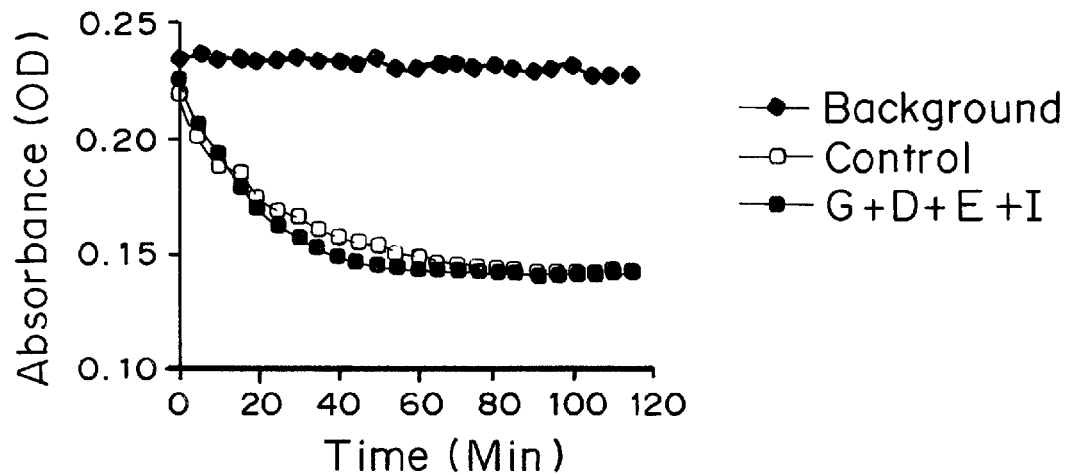
Figure 8E:
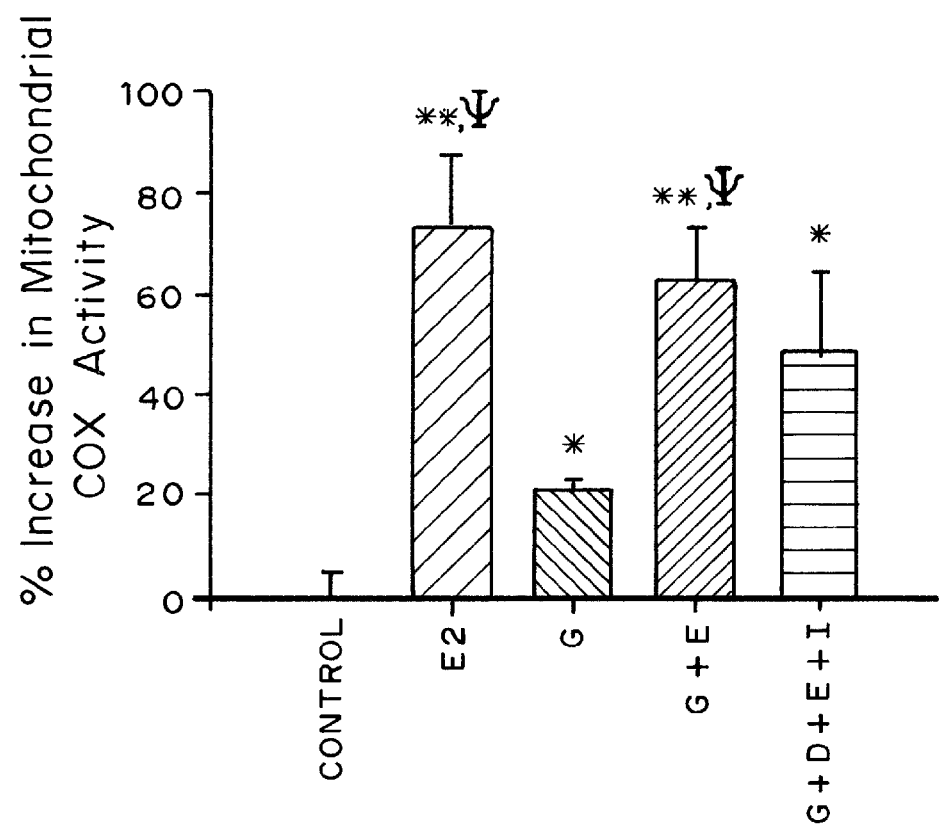

As shown in FIGS. 7A-7E, animals treated with 17β-estradiol (70 µg/kg/d for 2 days exhibited a significantly enhanced respiratory activity with an average increase of 42.7% (±7.9%) in the respiratory control ratio (RCR) measured in oxygen consumption (RCR=3.96±0.22), as compared to vehicle-treated control animals (RCR=2.78±0.09,  P<0.01). These data replicated our previous findings. Oxygen consumption in animals exposed to genistein alone (6 mg/kg/d for 2 d) did not exhibit a significant change (RCR=2.96±0.17) compared to control animals (FIG. 7B). In contrast, respiratory activity in animals exposed to the combination of G+D+E (6 mg/kg/d for 2 d, RCR 3.67±0.04, FIG. 7C) was significantly enhanced with an average increase of 32.2% (±1.5%) compared to control animals ( P<0.01). Similarly, exposure to the combination of G+D+E+I (6 mg/kg/d for 2 d, RCR=3.64±0.32, FIG. 7D) induced an average increase of 31.2% (±11.5%) compared to control animals (* P<0.05). Among four treatment groups, there was a statistically significant difference between 17β-estradiol and genistein (cp P<0.05) as well as between G+D+E and genistein treatment groups (φ P<0.05). The variance within the G+D+E+I-treated group prohibited a significant difference from genistein alone-treated group.

FIGS. 8A-8E show the effects on forebrain mitochondrial cytochrome oxidase (COX) activity in adult ovariectomized rats. Rats were given, once daily, 2 subcutaneous injections of the test compounds (or combinations). Rats were sacrificed 24 h later following the 2nd injection. Forebrain mitochondria were isolated followed by a spectrophotometric measurement of COX activity using an immunocapture method. Colorimetric absorbance at 550 nm was recorded every 5 min for 115 min. COX activity is presented as the initial rate of oxidation of reduced cytochrome c, and determined by calculating the initial slope between two time points (<20 min) within the linear region. (Upper Panel) Time-lapse change in absorbance; (Lower Panel) % increase in mitochondrial COX activity, n≥4; *P<0.05 and **P<0.01 compared to vehicle-treated control animals; $^\Psi$P<0.05 compared to genistein-treated animals. Combined formulations were composed of equivalent weight of individual phytoSERMs including E2: 17bestradiol; G: genistein; D: daidzein; E: equol; I: IBSO03569.

Consistent with previous reports, 17β-estradiol treatment (70 μg/kg/d for 2 d, FIG. 8E)) induced a significant increase (73.3±13.9%) in mitochondrial COX activity compared to vehicle-treated control animals (** P<0.01). In contrast to the lack of an effect on mitochondrial respiration, animals treated with genistein alone (6 mg/kg/d for 2 d) exhibited a moderate but statistically significant enhancement in COX activity (FIGS. 8B and 8E, 21.3±0.8% increase relative to control animals, * P<0.05). Similar to the data on respiration, animals treated with the combination of G+D+E (6 mg/kg/d for 2 d) or G+D+E+I (6 mg/kg/d for 2 d) induced an average increase of 62.7% (±10.8%, ** P<0.01) and 48.0% (±16.2%, * P<0.01), respectively, in COX activity as compared to vehicle-treated control animals (FIGS. 8C, 8D, and 8E. Among the four treatment groups, a statistically significant difference occurred between 17β-estradiol and genistein (φ P<0.05) as well as between G+D+E and genistein treatment groups (φ P<0.05). Consistent with the respiratory activity, there was no significant difference between G+D+E+I and genistein treatment groups.

Effect on Uterine Weight

Induction of proliferative responses and risk of cancers in reproductive tissues, associated with the currently available estrogen-containing HT, has been a major concern to women who receive this therapy. In the present study, the impact of the test phytoestrogen formulations on uterine growth was assessed by the weight of uteri excised at the time when animals were sacrificed. Wet weight was immediately recorded followed by air drying of uteri for 1 week followed by incubation at 70° C. overnight and subsequent determination of dry uterine weight.

Data shown in Table 4 revealed that as expected, treatment with 17β-estradiol (70 μg/kg/d for 2 d) induced a marked increase in both wet (120.2±25.1% increase compared with vehicle-treated control animals,  P<0.01) and dry uterine weight (76.7±15.6% increase compared with vehicle-treated control animals,  P<0.01). Treatment with genistein alone (6 mg/kg/d for 2 d, 12.9±8.0% and 6.5±7.7% increase in wet and dry weight, respectively, compared with control animals), the combination of G+D+E (6 mg/kg/d for 2 d, −6.1±0.9% and −10.3±0.1% increase in wet and dry weight, respectively, compared with control animals), or G+D+E+I (6 mg/kg/d for 2 d, 15.2±14.5% and 8.7±13.9% increase in wet and dry weight, respectively, compared with control animals), did not induce a significant impact on uterine weight. Although there was not a statistical significance, a trend toward a slightly declined uterine weight was observed in animals treated with the combination of G+D+E, but not in those treated with either genistein alone or the combination of G+D+E+I, as compared to vehicle-treated control animals.

TABLE 4

Effects on uterine weight in adult ovariectomized rats[A]

| Treatment | Wet Weight (mg) | Uterine Weight Increase (%)[B] | Dry Weight (mg) | Increase (%)[B] |
|---|---|---|---|---|
| Control Vehicle | 127.65 ± 10.75 | 0.00 ± 8.42 | 26.42 ± 2.45 | 0.00 ± 9.27 |
| 17β-Estradiol (70 μg/kg BW) | 281.06 ± 32.00**[D] | 120.23 ± 25.07**[D] | 46.70 ± 4.13**[D] | 76.14 ± 15.63**[D] |
| Genistein (6 mg/kg BW) | 144.11 ± 10.18 | 12.92 ± 7.97 | 28.14 ± 2.04 | 6.49 ± 7.71 |
| G + D + E (6 mg/kg BW)[C] | 199.84 ± 1.19 | −6.10 ± 0.93 | 23.71 ± 0.04 | −10.26 ± 0.13 |
| G + D + E + I (6 mg/kg BW)[C] | 146.99 ± 18.45 | 15.17 ± 14.46 | 28.73 ± 3.67 | 8.73 ± 13.90 |

[A] Adult ovariectomized rats were given, daily once, 2 subcutaneous injections of the test compounds (or combinations) (n ≥ 4 for each group). Rats were sacrificed 24 h later following the 2nd injection. Uteri were immediately excised and a wet weight was recorded. Uteri were then air dried for 1 hour followed by at 70° C. overnight, and the dry weight was recorded.
[B] Increase in uterine weight compared with vehicle-treated control animals and expressed as the percent of control (set as 0).
[C] Combined formulations were composed of equivalent weight of individual phytoSERMs included for a total amount of 6 mg/kg BW given to animals.
G: genistein;
D: daidzein;
E: equol; I: IBSO03569.
[D] **P < 0.01 compared to any other treatment groups.

Example 3

Figure 9A:
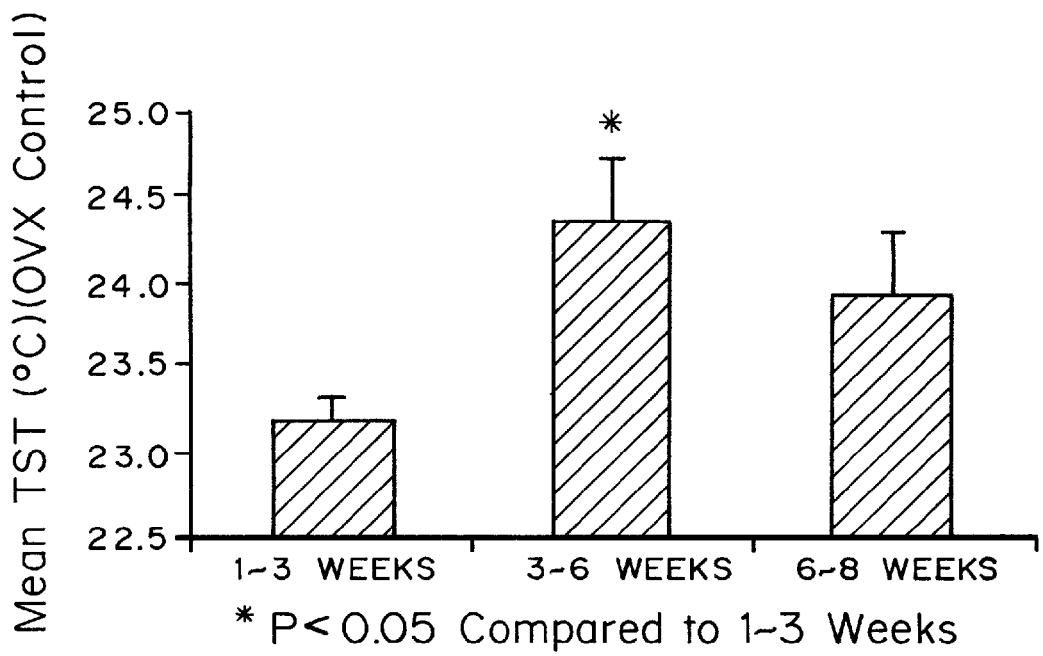
FIG. 9A is a graph showing that estrogen depletion by OVX in adult female mice induced a significant rise in the tail skin temperature (mean TST, ° C.) versus a sham-OVX control.
Figure 9B:
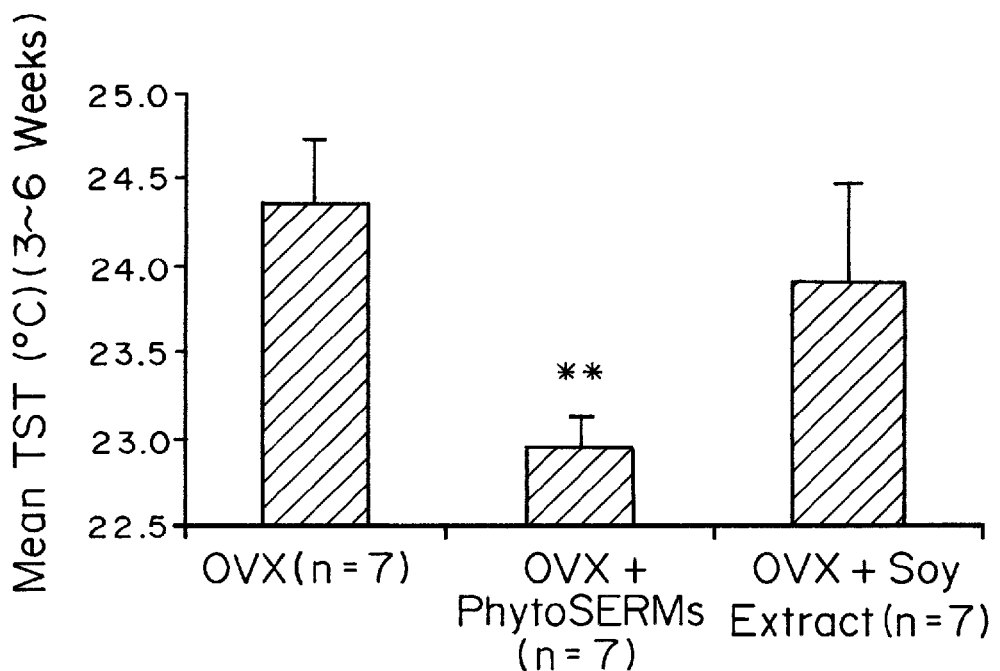
FIG. 9B is a graph showing that the tail skin temperature increase was prevented by the phytoSERMs (G+D+E)-containing diet, but not the soy extract diet.

PhytoSERMs Prevented Estrogen Depletion by Ovariectomy (OVX)-Induced Rise in Tail Skin Temperature (TST) in a Mouse Hot Flash Model Data shown in FIG. 9 demonstrate that estrogen depletion by OVX induced a significant rise in the tail skin temperature (TST) in mice treated with the control diet (FIG. 9A), which was prevented by the phytoSERMs-containing diet but not the soy extract diet (FIG. 9B). These data suggest the therapeutic potential of the phytoSERMs for preventing/treating menopausal hot flashes and possibly other symptoms.

Figure 10A:
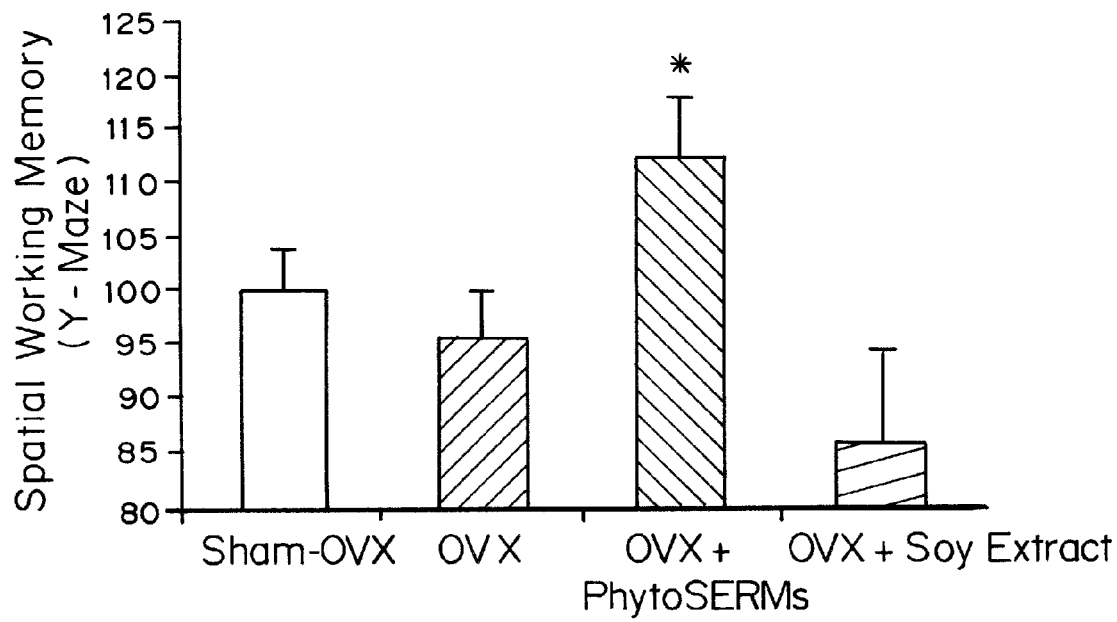
FIGS. 10A-10F are graphs showing that the phytoSERMs (G+D+E)-containing diet promoted spatial working memory function, neurotrophic/synaptic protein expression, and β-amyloid clearance against AD pathogenesis in ovariectomized adult female mice.
Figure 10B:
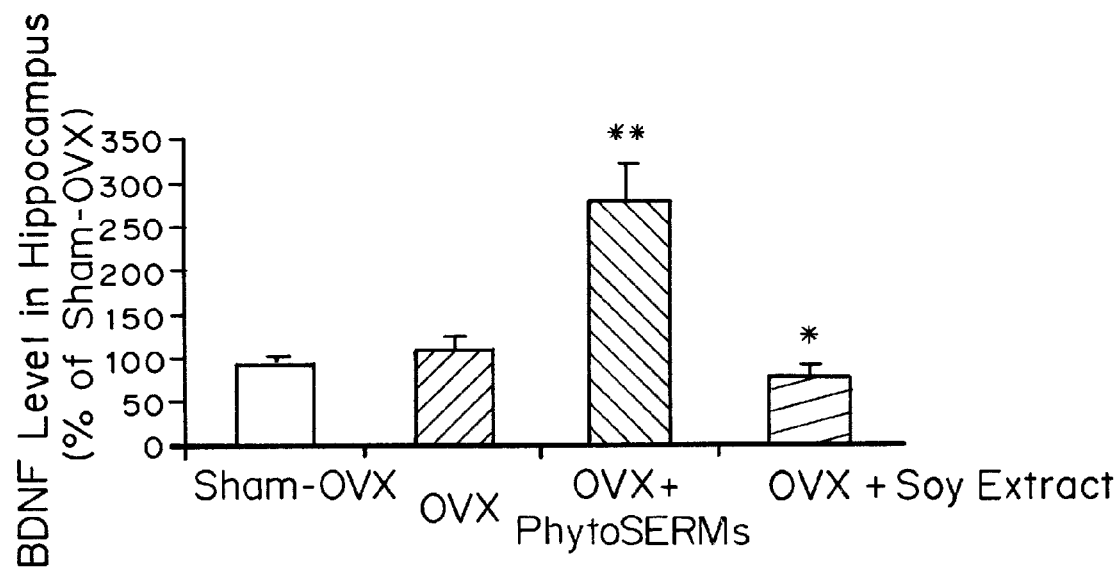
Figure 10C:
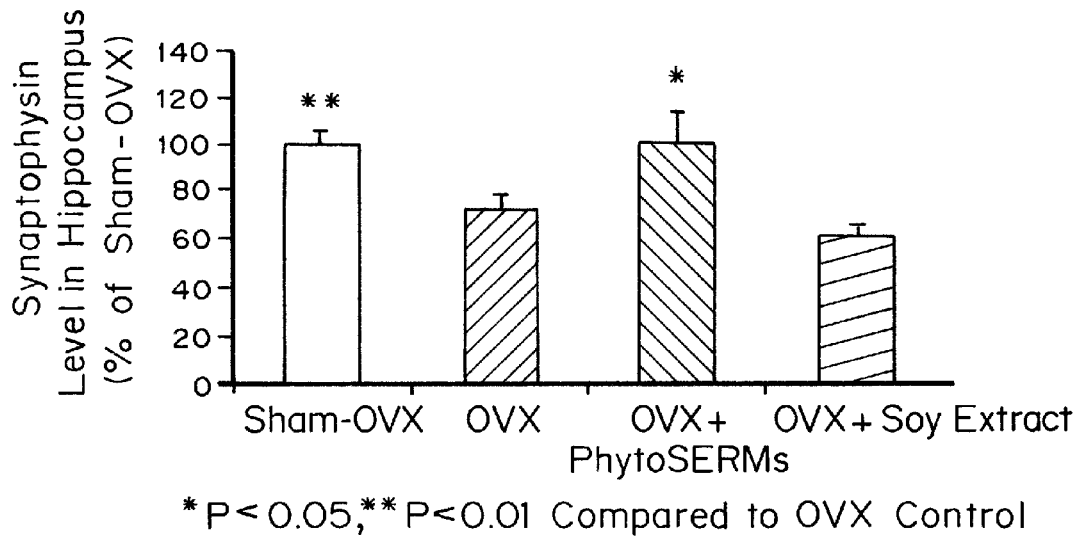
Figure 10D:
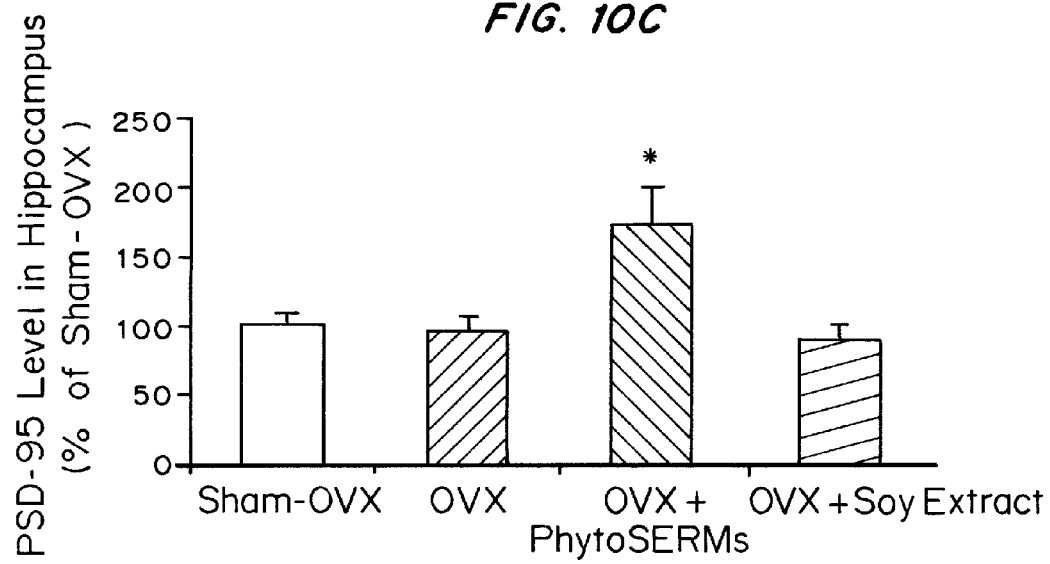
Figure 10E:
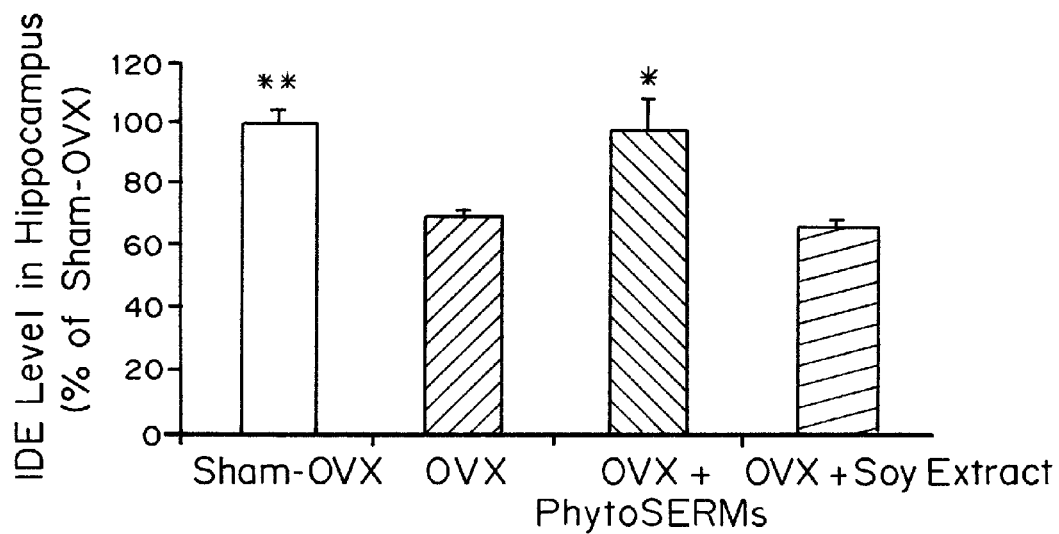
Figure 10F:
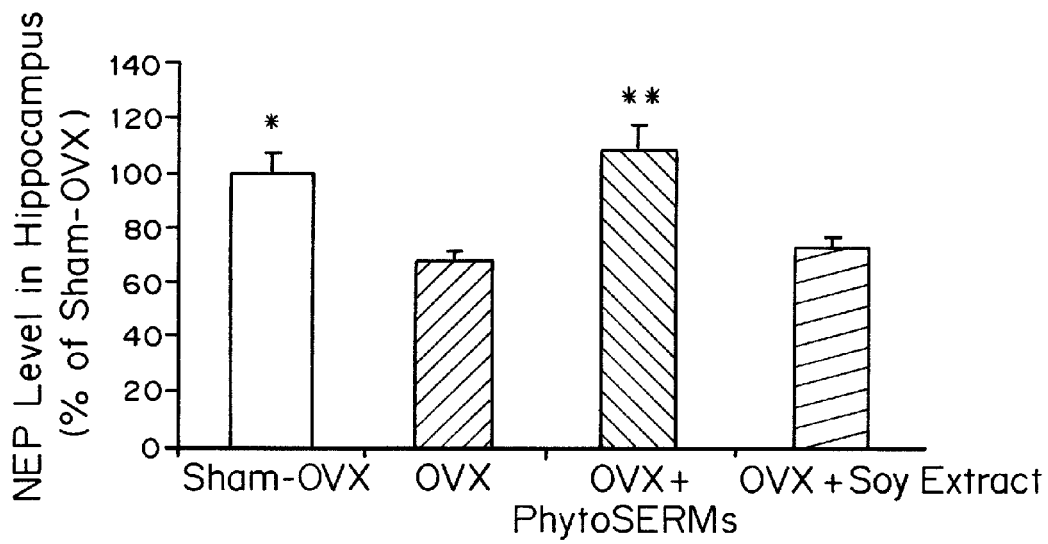

2. PhytoSERMs Promoted Spatial Working Memory Function, Neurotrophic/Synaptic Protein Expression and β-Amyloid Clearance Mechanism Against AD Pathogenesis in Female Mice Data shown in FIG. 10 demonstrate that in a Y-maze two-trial recognition test of spatial working memory function, OVX mice treated with the phytoSERMs-containing diet performed significantly better than OVX mice treated with the control diet (FIG. 10A). Consistently, Western blot analyses of the hippocampal protein samples derived from these animals revealed that the expression levels of proteins involved in neurotrophism and synapse formation, including the brain-derived neurotrophic factor (BDNF, FIG. 10B), the pre-synaptic protein synaptophysin (FIG. 10C), and the post-synaptic protein SPD-95 (FIG. 10D), in the hippocampal tissues of OVX mice treated with the phytoSERMs-containing diet were significantly higher than OVX mice treated with the control diet. Moreover, phytoSERMs diet prevented estrogen depletion by OVX-induced reduced expression of two β-amyloid-degrading enzymes, IDE (FIG. 10E) and NEP (FIG. 10F). In contrast, the soy extract diet either had no effect or a negative impact in both the behavioral task and on the associated mechanistic indicators. These data suggest the therapeutic potential of the phytoSERMs for preventing age-related cognitive decline and promoting brain neurotrophism and defense mechanisms against AD pathogenesis.

We claim:

1. A method for alleviating or preventing hot flashes, hair loss/thinning, cognitive decline associated with menopause, and combinations thereof in a patient comprising administering to the patient an effective amount of a formulation comprising three or more phytoestrogen compounds or analogues thereof that selectively bind to estrogen receptor beta and cross the blood brain barrier, the formulation not containing compounds that preferentially bind to estrogen receptor alpha, wherein
   the patient is a menopausal or post-menopausal woman;
   the three or more phytoestrogen compounds are selected from the group consisting of genistein, daidzein, equol, IBSO03569, and combinations thereof, and are administered in an effective amount from about 0.1 mg/kg/day to about 20 mg/kg/day; and
   the phytoestrogen compounds are more effective in combination than the same amount of the individual phytoestrogen compounds.

2. The method of claim 1, wherein the formulation comprises genistein, daidzein, and equol.

3. The method of claim 1, wherein the formulation comprises genistein, daidzein, equol, and IBS003569.

4. The method of claim 1, wherein the phytoestrogen compounds are administered in an effective amount from about 1 mg/kg/day to about 10 mg/kg/day.

5. The method of claim 1, wherein the formulation is administered in a single dose or in divided doses.

6. The method of claim 1, wherein the phytoestrogen compounds are formulated for modified release.

7. The method of claim 6, wherein modified release is selected from the group consisting of sustained release, delayed release, pulsatile release, and combinations thereof.

* * * * *